United States Patent
Mitsuhashi et al.

(10) Patent No.: US 10,266,895 B2
(45) Date of Patent: Apr. 23, 2019

(54) EXOSOMES AND MICROVESICLES IN INTESTINAL LUMINAL FLUIDS AND STOOL AND USE OF SAME FOR THE ASSESSMENT OF INFLAMMATORY BOWEL DISEASE

(71) Applicants: HITACHI CHEMICAL COMPANY LTD., Tokyo (JP); Hitachi Chemical Co. America, Ltd., Cupertino, CA (US); BETH ISRAEL DEACONESS MEDICAL CENTER, Boston, MA (US)

(72) Inventors: Masato Mitsuhashi, Irvine, CA (US); Alan C. Moss, Dover, MA (US)

(73) Assignees: Hitachi Chemical Company Ltd., Tokyo (JP); Hitachi Chemical Co. America, Ltd., San Jose, CA (US); Beth Israel Deaconess Medical Center, Boston, MA (US)

( * ) Notice: Subject to any disclaimer, the term of this patent is extended or adjusted under 35 U.S.C. 154(b) by 486 days.

(21) Appl. No.: 14/931,716

(22) Filed: Nov. 3, 2015

(65) Prior Publication Data

US 2016/0122823 A1    May 5, 2016

Related U.S. Application Data

(60) Provisional application No. 62/075,683, filed on Nov. 5, 2014.

(51) Int. Cl.
  *C12Q 1/68*  (2018.01)
  *C12Q 1/6883*  (2018.01)
  *C12Q 1/6806*  (2018.01)

(52) U.S. Cl.
  CPC ......... *C12Q 1/6883* (2013.01); *C12Q 1/6806* (2013.01); *C12Q 2600/158* (2013.01)

(58) Field of Classification Search
  None
  See application file for complete search history.

(56) References Cited

U.S. PATENT DOCUMENTS

| | | | |
|---|---|---|---|
| 3,583,627 A | 6/1971 | Wilson | |
| 4,895,706 A | 1/1990 | Root et al. | |
| 4,925,572 A | 5/1990 | Pall | |
| 5,139,685 A | 8/1992 | de Castro et al. | |
| 5,372,945 A | 12/1994 | Alchas et al. | |
| 5,647,990 A | 7/1997 | Vassarotti | |
| 5,733,449 A | 3/1998 | Bowers et al. | |
| 5,747,256 A | 5/1998 | Yan et al. | |
| 6,329,179 B1 | 12/2001 | Kopreski | |
| 6,375,855 B1 | 4/2002 | Vassarotti | |
| 6,964,850 B2 | 11/2005 | Bevilacqua et al. | |
| 7,026,121 B1 | 4/2006 | Wohlgemuth et al. | |
| 7,608,402 B2 | 10/2009 | Li et al. | |
| 7,741,023 B2 | 6/2010 | Mitsuhashi | |
| 7,745,180 B2 * | 6/2010 | Mitsuhashi | C12N 1/066 435/6.1 |
| 8,567,609 B2 | 10/2013 | Landrigan et al. | |
| 8,591,391 B2 | 11/2013 | Chavarria et al. | |
| 9,012,615 B2 | 4/2015 | Mitsuhashi et al. | |
| 9,458,496 B2 | 10/2016 | Mitsuhashi et al. | |
| 9,662,649 B2 | 3/2017 | Mitsuhashi et al. | |
| 9,719,129 B2 | 8/2017 | Mitsuhashi et al. | |
| 9,790,542 B2 | 10/2017 | Mitsuhashi et al. | |
| 2002/0011450 A1 | 1/2002 | Kelly et al. | |
| 2003/0203453 A1 | 10/2003 | Leonard | |
| 2004/0029124 A1 | 2/2004 | Zohlnhofer et al. | |
| 2004/0072193 A1 | 4/2004 | Mitsuhashi | |
| 2004/0203037 A1 | 10/2004 | Lo et al. | |
| 2004/0258570 A1 | 12/2004 | Beebe et al. | |
| 2004/0265864 A1 | 12/2004 | Mitsuhashi | |
| 2006/0144790 A1 | 7/2006 | Kelly et al. | |
| 2007/0254351 A1 | 11/2007 | Abrignani et al. | |
| 2007/0264272 A1 | 11/2007 | Perreault et al. | |
| 2008/0009009 A1 | 1/2008 | Mitsuhashi | |
| 2008/0015162 A1 | 1/2008 | Bhanot et al. | |
| 2008/0025967 A1 | 1/2008 | Doi et al. | |

(Continued)

FOREIGN PATENT DOCUMENTS

| | | |
|---|---|---|
| JP | 1997-067336 | 3/1997 |
| WO | WO 1993/19831 | 10/1993 |

(Continued)

OTHER PUBLICATIONS

"Binding Assays with Membranes," Jan. 1, 2006, Protein Biochemistry and Protoeomics, Elsevier, pp. 37-39.
Absolute Quantitation Using Standard Curve Getting Guide, Applied Biosystems, pp. i-viii and 1-80, Jun. 2010, printed from http://www3.appliedbiosystems.com/cms/groups/mcb_support/documents/generaldocuments/cms_032176.pdf.
Akoglu et al.: "Interleukin-2 in CD8+ T cells correlates with Banff score during organ rejection in liver transplant recipients," Clin Exp Med (2009) 9:259-262.
Alvarez ML, et al., Comparison of protein, microRNA, and mRNA yields using different methods of urinary exosome isolation for the discovery of kidney disease biomarkers. Kidney Int. 82: 1024-1032, 2012.

(Continued)

*Primary Examiner* — Samuel C Woolwine
(74) *Attorney, Agent, or Firm* — Knobbe Martens Olson & Bear LLP

(57) ABSTRACT

The present disclosure relates to methods of collecting intestinal luminal fluid (ILF) exosomes and microvesicles (EMV) and isolating corresponding mRNA in order to diagnose and treat inflammatory bowel diseases (IBD). In particular, certain embodiments relate to the method of capturing EMV from ILF applied to a filter device that is capable of capturing EMV. Nucleic acids such as mRNA can be isolated from the EMV using an oligo(dT)-coated plate designed to accommodate the filter device and then used for further molecular analysis. Quantification of the collected nucleic acids may then be used in the diagnosis and/or treatment of IBD.

17 Claims, 7 Drawing Sheets
Specification includes a Sequence Listing.

(56) References Cited

U.S. PATENT DOCUMENTS

| | | |
|---|---|---|
| 2008/0299558 A1 | 4/2008 | Kondo et al. |
| 2008/0188816 A1 | 8/2008 | Shimazaki et al. |
| 2008/0233573 A1 | 9/2008 | Storm et al. |
| 2008/0268429 A1 | 10/2008 | Pietrzkowski |
| 2009/0011410 A1 | 1/2009 | Mitsuhashi |
| 2009/0023149 A1 | 1/2009 | Knudsen |
| 2009/0149333 A1 | 6/2009 | Knudsen et al. |
| 2009/0258379 A1 | 10/2009 | Klein et al. |
| 2010/0027315 A1 | 2/2010 | Kim |
| 2010/0113290 A1 | 5/2010 | Klass et al. |
| 2010/0196426 A1 | 8/2010 | Skog |
| 2010/0203529 A1 | 8/2010 | Kuslich et al. |
| 2010/0143898 A1 | 10/2010 | Kutyavin |
| 2011/0143348 A1 | 6/2011 | Tomigahara et al. |
| 2011/0171647 A1 | 7/2011 | Tomigahara et al. |
| 2011/0189674 A1 | 8/2011 | Tomigahara et al. |
| 2011/0195426 A1 | 8/2011 | Russo |
| 2011/0223583 A1 | 9/2011 | Gordon et al. |
| 2012/0211566 A1 | 8/2012 | Hensel et al. |
| 2012/0264628 A1 | 10/2012 | Okamoto et al. |
| 2013/0089855 A1 | 4/2013 | Mitsuhashi |
| 2013/0165338 A1 | 6/2013 | Schmidt-Ott et al. |
| 2013/0172208 A1* | 7/2013 | Mitsuhashi .......... C12Q 1/6876 506/9 |
| 2013/0323751 A1 | 12/2013 | Singbartl et al. |
| 2013/0337462 A1 | 12/2013 | Mergemeier |
| 2014/0099649 A1 | 4/2014 | Mitsuhashi |
| 2014/0148348 A1 | 5/2014 | Kuslich |
| 2014/0148350 A1 | 5/2014 | Spetzler |
| 2014/0194613 A1 | 7/2014 | Skog et al. |
| 2015/0141634 A1 | 5/2015 | Mitsuhashi |
| 2015/0275301 A1 | 10/2015 | Mitsuhashi et al. |
| 2016/0074860 A1 | 3/2016 | Mitsuhashi |
| 2016/0222456 A1 | 8/2016 | Yamamoto |
| 2016/0237496 A1 | 8/2016 | Mitsuhashi |
| 2017/0184575 A1 | 6/2017 | Murakami |
| 2017/0335397 A1 | 11/2017 | RamachandraRao et al. |

FOREIGN PATENT DOCUMENTS

| | | |
|---|---|---|
| WO | WO 2002/057414 | 7/2002 |
| WO | WO 2006/045053 | 4/2006 |
| WO | WO 2008/092993 | 8/2008 |
| WO | WO 2009/015357 | 1/2009 |
| WO | WO 2009/057695 | 5/2009 |
| WO | WO 2009/070442 | 6/2009 |
| WO | WO 2009/100029 | 8/2009 |
| WO | WO 2010/056337 | 5/2010 |
| WO | WO 2010/086163 | 8/2010 |
| WO | WO 2011/031892 | 3/2011 |
| WO | WO 2011/084333 | 7/2011 |
| WO | WO 2011/100458 | 8/2011 |
| WO | WO 2011/112961 | 9/2011 |
| WO | WO 2011/127219 | 10/2011 |
| WO | WO 2011/156734 | 12/2011 |
| WO | WO 2011/156763 | 12/2011 |
| WO | WO 2012/102963 | 8/2012 |
| WO | WO 2012/170037 | 12/2012 |
| WO | WO 2013/012947 | 1/2013 |
| WO | WO 2013/028788 | 2/2013 |
| WO | WO 2013/041913 | 3/2013 |
| WO | WO 2013/043922 | 3/2013 |
| WO | WO 2013/134786 | 9/2013 |
| WO | WO 2013/188846 | 12/2013 |

OTHER PUBLICATIONS

Anders S, et al., Count-based differential expression analysis of RNA sequencing data using R and Bioconductor. Nat. Protoc. 8: 1765-1786, 2013.
Anglicheau et al., "Discovery and Validation of a Molecular Signature for the Noninvasive Diagnosis of Human Renal Allograft Fibrosis," NIH Public Access, Author Manuscript, Transplantation Jun. 15, 2012; 93(11): 1136-1146.
Arteaga et al., Endothelial microparticles and platelet and leukocyte activation in patients with the metabolic syndrome, Am J Cardiol, vol. 98:70-74 (2006).
Bachmann et al., Renal effects of Tamm-Horsfall protein (uromodulin) deficiency in mice, Am J Physiol, Renal Physiol, 288:F559-567 (2005).
Bailey et al., : "Transplanted adult hematopoietic stems cells differentiate into functional endothelial cells," The American Society of Hematology, Plenary paper, 2004.
Bakris, GL., Recognition, pathogenesis, and treatment of different stages of nephropathy in patients with type 2 diabetes mellitus. Mayo Clinic Proceedings, vol. 86, No. 5, pp. 444-456, May 2011.
Baldi P, et al., A Bayesian framework for the analysis of microarray expression data: regularized t-test and statistical inferences of gene changes. Bioinformatics 17: 509-519, 2001.
Bangs Laboratories Tech Note 204, Adsorption to Microspheres, Apr. 9, 2008 (printed from Internet Jan. 18, 2012 from <http://www.bangslabs.com/sites/default/files/bangs/docs.pdf/204.pdf>).
Barnett et al., Angiotensin-Receptor Blockade versus Converting-Enzyme Inhibition in Type 2 Diabetes and Nephropathy, N Eng J Med (2004) 351:1952-61.
Beltrami, et al.: "Analysis of urinary microRNAs in chronic kidney disease: Figure1," Biochemical Society Transactions, vol. 12, No. 0. 4, Aug. 1, 2012, pp. 4-879.
Bio Scientific, "ExoMir Kit Manual", Catalog 5145, www.yumpu.com/en/document/view/30138118/exomirtm-kit-manual-nordic-biosite/2, Feb. 17, 2015.
Botteman MF, et al., The health economics of bladder cancer: a comprehensive review of the published literature. PharmacoEconomics 21: 1315-1330, 2003.
Brushi M, et al., Glomerular Autoimmune Multicomponents of Human Lupus Nephritis In Vivo: α-Enolase and Annexin Al. J. Am. Soc. Nephrol. 25: 2483-2498, 2014.
Chapter 6: Transplantation, 2014 USRDS Annual Data Report, vol. 2 ESRD, pp. 153-162.
Chen et al., Microfluidic isolation and transcriptome analysis of serum microvesicles, J Royal Soc of Chem (2010) vol. 10:505-511.
Chen et al., Inhibition of Ultraviolet B-Induced c-fos Gene Expression and p38 Mitogen-Activated Protein Kinase Activation by (−)-Epigallocatechin Gallate in a Human Keratinocyle Cell Line, Molecular Carcinogenesis (1999) vol. 24(2):79-84.
Cheruvanky et al.: Rapid isolation of urinary exosomal biomarkers using a nanomembrane ultrafiltration concentrator, Am J. Physio. Renal. Physiol 292: F1657-F1661, 2007.
Common Cancer Types [Internet]. Natl. Cancer Inst. Available from: http://www.cancer.gov/types/common-cancers [cited Aug. 6, 2015].
Conde-Vancells et al., Candidate biomarkers in exosome-like vesicles purified from rat and mouse urine samples, Proteomics Clin Appl 4(4):416-25 (2010).
Cutillas et al., The urinary proteome in Fanconi syndrome implies specificity in the reabsorption of proteins by renal proximal tubule cells, Am J Physio Renal Physiol (2004) vol. 287(3):353-364.
Dennis et al., Identification from public data of molecular markers of adenocarcinoma characteristic of the site of origin, Cancer Res, vol. 62(21):5999-6005 (2002).
Dimuccio et al., "Urinary CD133+ Extracellular Vesicles Are Decreased in Kidney Transplanted Patients with Slow Graft Function and Vascular Damage," Plos One, vol. 9, No. 8, e104490, pp. 1/11-11/11, Aug. 6, 2014.
Duffield et al. Simultaneous determination of multiple mRNA levels utilizing MALDI-TOF mass spectrometry and biotinylted dideoxynucleotides. RNA, vol. 16, pp. 1285-1291, (2010).
Enard et al., Intra- and Interspecific Variation in Primate Gene Expression Patterns, Science (2002) vol. 296:340.
Erusalimsky et al.: A Glass Fiber/Diethylaminoethyl Double Filter Binding Assay That Measures Apoptotic Internucleosomal DNA Fragmentation, Analytical Biochemistry 242, 187-196 (1996) Article No. 0452.
Evseenko, et al.: "Mapping the first stages of mesoderm commitment during differentiation of human embryonic stem cells," PNAS, vol. 107, No. 31, 13742-13747, Aug. 3, 2010.

(56) References Cited

OTHER PUBLICATIONS

Fang DY, et al., Exosomes and the kidney: Blaming the messenger. Nephrology 18: 1-10, 2013.
Feng, et al., "Research issues and strategies for genomic and proteomic biomarker discovery and validation: a statistical perspective," Pharmacogenomics, vol. 5, No. 6, pp. 709-719, 2004.
Ferguson et al.: Vesicular Localization and Activity-Dependent Trafficking of Presynaptic Choline Transponders, The Journal of Neuroscience, Oct. 29, 2003, 23(30):9697-9699.
Fuchs et al., "An Exploratory Evaluation of the Utility of Transcriptional and Urinary Kidney Injury Biomarkers for the Prediction of Aristolochic Acid-Induced Renal Injury in Male Rats," Veterinary Pathology, 2014, vol. 51 (3) 680-694.
Gallagher et al. "Unit 10.8: Immunoblotting and Immunodetection" in Current Protocols in Molecular Biology, Supplement 66, pp. 10.8.1-10.8.24, (2004).
Gene Cards DEFA3 Gene, first internet archive Aug. 7, 2010, pp. 1-14.
Golub, et al.: "Molecular Classification of Cancer: Class Discovery and Class Prediction by Gene Expression Monitoring," Science, vol. 286, pp. 531-537, Oct. 1999.
Gonzales et al., Chapter 6: Isolation and Purification of Exosomes in Urine in Alex J. Rai (ed.), The Urinary Proteome: Methods and Protocols, Methods in Molecular Biology, vol. 641, pp. 89-99, 2010.
Gonzales et al., Large-scale proteomics and phosphoproteomics of urinary exosomes, J Am Soc Nephrol, 20(2):363-79 (2009).
Grams et al.: "Fluid Balance, Diuretic Use, and Mortality in Acute Kidney Injury," Clin J AM Soc Nephrol 6:966-973, Mar. 10, 2011.
Grant et al., A filtration-based protocol to isolate human plasma membrane-derived vesicles and exosomes from blood plasma. Journal of Immunological Methods, vol. 371, pp. 143-151, Jun. 30, 2011.
Guo et al., Surfactant protein gene A, B, and D marker alleles in chronic obstructive pulmonary disease of a Mexican population, Eur Respir J, 18(3):482-90 (2001).
Haas et al., Patient characteristics associated with successful mobilizing and autografting of peripheral blood progenitor cells in malignant lymphoma, Blood (1994) vol. 83(12):3787-3794.
Harada and Mitsuhashi, "Assessment of post-transplant kidney function by measuring glomerulus and tubule specific mRNAs in urine exosome," American Journal of Transplantation, vol. 12, Supp. 3, pp. 369-370, Abstract No. 1158, May 2012.
Hashem, Biochemical and expression studies on Acquaporin 9 (AQP9) in wild and AQP9 knockout mice, Veterinarski Archiv (2010) vol. 80(1):93-112.
Hess et al., The hydroxylamine of sulfamethoxazole synergizes with FK506 and cyclosporine A, inhibiting T-Cell proliferation, J Pharm & Exp Tech (1996) vol. 281(1):540-548.
Hewitt et al., Discovery of Protein Biomarkers for Renal Diseases, J Am Soc Nephrol (2004) vol. 15(7):1677-1689.
Hoorn et al., Prospects for urinary proteomics: exosomes as a source of urinary biomarkers, Nephrology, 10:283-290 (2005).
Hornbeck, et al., "Unit 11.2: Enzyme-Linked Immunosorbent Assays (ELISA)" in Current Protocols in Biology, Supplement 15, pp. 11.2.1-11.2.22, (1991).
Hotfilder et al., Def-2, -3, -6 and -8, novel mouse genes differentially expressed in the haemopoietic system, Brit J Haematol (1999) vol. 106:335-344.
Hunter et al., Detection of microRNA expression in human peripheral blood microvesicles, PLoS One 3:e3694 (2008).
Ide et al., "Transduction of Murine Hematopoietic Stem Cells and In Vivo Selection of Gene-Modified Cells," Methods in Molecular Biology, vol. 433, vol. 1: Production and In Vivo Applications of Gene Transfer Vectors, 2008, pp. 213-228.
Ito et al., Myeloid Reconstution. Serum stem cell growth factor for monitoring hematopoietic recovery following stem cell transplantation, Bone Marrow Transplantation (2003) vol. 32:391-398.
Jimenez et al., Endothelial microparticles released in thrombotic thrombocytopenic purpura express von Willibrand factor and markers of endothelial activation, Br J Haemat (2003) vol. 123(5):896-902.
Keller et al., "Body fluid derived exosomes as a novel template for clinical diagnostics," Journal of Translational Medicine, vol. 9, 86, Jun. 2011, printed as pp. 1/9-9/9.
Klein et al., Ex-Vivo Assessment of Candidate Anti-Inflammatory Agents in the Treatment of Gram Negative Sepsis, Immun & Infec Dis (1994) vol. 4(1):33-35.
Koga et al., Purification, characterization and biological significance of tumor-derived exosomes, Anticancer Res, 25(6A):3703-7 (2005).
Kroese et al., "Genetic tests and their evaluation: Can we answer the key questions?" Genetics in Medicine, vol. 5, No. 6, pp. 475-480, 2004.
Labsource: Whatman Glass Microfiber Filters, printed from internet Dec. 12, 2009 2011:<URL:http://www.labsource.com/Catalog/Group.aspx?GroupID=82>] p. 1.
Lebedev et al., Oligonucleotides containing 2-aminoadenine and 5-methylcyotsine are more effective as primers for PCR amplification than their normal nonmodified counterparts, Gen Anal (1996) vol. 13(1):15-21.
Lescuyer et al., Proteomics: Clinical Applications (2008) vol. 2(7-8):1008.
Liu et al., Transcriptome profiling and sequencing of differentiated human hematopoietic stem cells reveal lineage-specific expression and alternative splicing of genes, Physiol Genomics 43:1117-1134, 2011.
Lo, et al., "Defining the relationship between average glucose and HbA1c in patients with type 2 diabetes and chronic kidney diabetes," Diabetes Research and Clinical Practice, vol. 104, pp. 84-91, 2014, on line Feb. 3, 2014.
Lu et al., "Tracking single hematopoietic stem cells in vivo using high-throughput sequencing in conjunction with viral genetic barcoding," Nature Biotechnology 29, 928-933 (2011) and supplementary data.
Lucendo et al., Treatment with topical steroids downregulates IL-5, eotaxin-1/CCL11, and eotaxin-3/CCL26 gene expression in eosinophilic esophagitis, Am J Gastro 103(9):2184-93 (2008).
Luo et al., RANTES stimulates inflammatory cascades and receptor modulation in murine astrocytes, 39(1):19-30 (2002).
Masyuk, et al.: "Exosomes in the pathogenesis, diagnostics and therapeutics of liver diseases," Journal of Hematology 2013 vol. 59, 621-625.
Mathivanan, et al.: "ExoCarta 2012: database of exosomal proteins, RNA and lipids," Nucleic Acids Research, vol. 40, No. D1, Oct. 11, 2011, pp. D1241-D1244.
Mathivanan, et al.: "Exosomes: Extracellular Organelles Important in Intercellular Communication," J of Proteomics 73(10)1907-20, 2010.
Melé M, et al., The human transcriptome across tissues and individuals. Science 348: 660-665, 2015.
Mi H, et al., Large-scale gene function analysis with the PANTHER classification system. Nat. Protoc. 8: 1551-1566, 2013.
Mikkola and Orkin, "The journey of developing hematopoietic stem cells," Development 133, 3733-3744 (2006).
Millàn, et al.: "Intracellular IFN-Y and IL-2 expression monitoring as surrogate markers of the risk of acute rejection and personal drug response in de novo liver transplant recipients," Cytokine 61 (2013) 556-564.
Miranda et al., Nucleic acids within urinary exosomes/microvesicles are potential biomarkers for renal disease, Kidney Intl (2010) vol. 78(2):191-199.
Mitchell et al., Can urinary exosomes act as treatment response markers in prostate cancer? J Transl Med, 12:7:4 (2009).
Mitsuhashi et al., Quantification of mRNA in Whole Blood by Assessing Recovery of RNA and Efficiency of cDNA Synthesis, Clin Chem (2006) vol. 52(4):634-642.
Mitsuhashi, Ex vivo simulation of leukocyte function: Stimulation of specific subset of leukocytes in whole blood followed by the measurement of function-associated nRNAs, J Immun Meth (2010) vol. 363(1):95-100.

(56) References Cited

OTHER PUBLICATIONS

Muller, Gunter: "Microvesicles/exosomes as potential novel biomarkers of metabolic diseases," Diabetes, Metabolic Syndrome and Obesity: Targets and Therapy, Aug. 1, 2012, p. 247.

Murakami et al.: "Development of Glomerulus-, Tubuel-, and Collecting Duct-Specific mRNA Assay in Human Urinary Exosomes and Microvesicles," PLOS ONE vol. 9, Oct. 2014, pp. 1-10.

Nilsson et al., Prostate cancer-derived urine exosomes: a novel approach to biomarkers for prostate cancer, Br J Cancer 100:1603-1607 (2009).

Notterman et al., in Microarrays and Cancer Research (2002) Warrington et al. (eds.) pp. 81-111 at pp. 81-82.

Obeidat, et al., "Post-transplant nuclear renal scans correlate with renal injury biomarkers and early allograft outcomes," Nephrol Dial Transplant (2011) 26: 3038-3045.

Ogura, et al., "Potential amelioration of upregulated renal HIF-1alpha-endothelin-1 system by landiolol hydrochloride in a rat model of endotoxemia," Life Sciences 1 18 (2014) 347-356.

Olszewska-Pazdrak et al., Cell-specific expression of RANTES, MCP-1, and MIP-1 alpha by lower airway epithelial cells and eosinophils infected with respiratory syncytial virus, J Virol, 72(6):4756-64 (1998).

OPTN: Organ Procurement and Transplantation Network—OPTN [Internet]. 2015 Available from: http://optn.transplant.hrsa.gov/ [cited Jun. 27, 2015].

Patterson, SD. "Unit 10.22: Protein Identification and Characterization by Mass Spectrometry" in Current Protocols in Molecular Biology, Supplement 41, pp. 10.22.1-10.22.24, (1998).

Peake et al., "A comparison of the ability of levels of urinary biomarker proteins and exosomal mRNA to predict outcomes after renal transplantation," PLoS One, Jun. 11, 2014, vol. 9, No. 2, e98644, pp. 1-7.

Pepe, et al, "Phases of Biomarker Development for Early Detection of Cancer," Journal of the National Cancer Institute, vol. 93, No. 14, pp. 1054-1061, Jul. 2001.

Perez A, et al., A Pilot Study on the Potential of RNA-Associated to Urinary Vesicles as a Suitable Non-Invasive Source for Diagnostic Purposes in Bladder Cancer. Cancers 6: 179-192, 2014.

Pisitkun et al., "Application of systems biology principles to protein biomarker discovery: urinary exosomal proteome in renal transplantation," Proteomics Clin Appl, Jun. 29, 2012, vol. 6, No. 5-6, pp. 268-278.

Pisitkun et al., Discovery of urinary biomarkers, Mol Cell Proteomics, 5(10):1760-71 (2006).

Pisitkun et al., Identification and proteomic profiling of exosomes in human urine, Proc Natl Acad Sci USA, 101:13368-73 (2004).

Post et al., Demonstration of the presence of independent pre-osteoblastic and pre-adipocytic cell populations in bone marrow-derived mesenchymal stem cells, Bone, 43(1):32-9 (2008).

Properzi F, et al., Exosomes: the future of biomarkers in medicine. Biomark. Med. 7: 769-778, 2013.

Pusztai et al.: "Clinical trial design for microarray predictive marker discovery and assessment," Annals of Oncology 15: 1731-1737, 2004.

R Core Team: R: The R Project for Statistical Computing [Internet]. R Lang. Environ. Stat. Comput. R Found. Stat. Comput. Vienna Austria. Available from: http://www.r-project.org/ [cited Jun. 15, 2015].

Rappa et al., The stem cell-associated antigen CD133 (Prominin-1) is a molecular therapeutic target for metastatic melanoma, Stem Cells, 26:3008-17 (2008).

Reeve J, et al., Molecular Diagnosis of T Cell-Mediated Rejection in Human Kidney Transplant Biopsies. Am. J. Transplant. 13: 645-655, 2012.

Roedder S, et al., The kSORT Assay to Detect Renal Transplant Patients at High Risk for Acute Rejection: Results of the Multicenter AART Study. PLoS Med 11: e1001759, 2014.

Sartorius Stedim Biotech., Ultrafiltration & Protein Purification Products. Fisher Scientic, pp. 1-96, Mar. 2011.

Savage, et al., "New Prognostic Markers: The Pathway from Research to Clinical Practice," Grand rounds Urol. Aug. 8, 2009(3): 7-13.

Sellam et al., Increased levels of circulating microparticles in primary Sjögren's syndrome, systemic lupus erythematosus and rheumatoid arthritis and relation with disease activity, Arthritis Res Ther 11(5):R156 (2009).

Sellarés J, et al., Molecular Diagnosis of Antibody-Mediated Rejection in Human Kidney Transplants. Am. J. Transplant. 13: 971-983, 2012.

Shipman, et al., "Effect of chronic kidney disease on A1C in individuals being screened for diabetes," Primary Care Diabetes 9 (2014) 142-146.

Simpson et al., Proteomic profiling of exosomes: current perspectives, Proteomics 8(19):4083-99 (2008).

Sing T, et al., ROCR: visualizing classifier performance in R. Bioinformatics 21: 3940-3941, 2005.

Smalley et al., Isolation and identification of potential urinary microparticle biomarkers of bladder cancer, J Proteome Res 7:2088-96 (2008).

Smith ZL, et al., Urinary markers for bladder cancer. F1000Prime Rep. [Internet] 5: 2013 Available from: http://www.ncbi.nlm.nih.gov/pmc/articles/PMC3702217/ [cited Aug. 17, 2015].

Stahlberg et al., Properties of the reverse transcription reaction in mRNA quantification. Clinical Chemistry, vol. 50, No. 3, pp. 509-515, 2004.

Strausberg et al., Reading the Molecular Signatures of Cancer, Microarrays & Cancer Res (2002) pp. xi-xvi.

Suthanthiran M, et al., Urinary-Cell mRNA Profile and Acute Cellular Rejection in Kidney Allografts. N. Engl. J. Med. 369: 20-31, 2013.

Tankova, et al., "Assessment of HbA1c as a diagnostic tool in diabetes and prediabetes," Acta Diabetol (2012) 49:371-378.

Taub et al., Role of biomarkers in the diagnosis and prognosis of acute kidney injury in patients with cardiorenal syndrome, Expert Review of Cardiovascular Therapy, vol. 10, No. 5, pp. 657-667, May 1, 2012.

Taylor et al., MicroRNA signatures of tumor-derived exosomes as diagnostic biomarkers of ovarian cancer, Gynecol Oncol 110(1):13-21 (2008).

The Cancer Genome Atlas Research Network: Comprehensive molecular characterization of urothelial bladder carcinoma. Nature [Internet] advance online publication: 2014 Available from: http://www.nature.com/nature/journal/vaop/ncurrent/full/nature12965.html [cited Feb. 21, 2014].

Théry C, et al., Exosomes: composition, biogenesis and function. Nat. Rev. Immunol. 2: 569-579, 2002.

Théry C, et al., Membrane vesicles as conveyors of immune responses. Nat. Rev. Immunol. 9: 581-593, 2009.

Théry et al., Isolation and characterization of exosomes from cell culture supernatants and biological fluids, Chapter 3, Curr Protoc Cell Biol, Unit 3.22 (2006).

Tockman et al., Considerations in bringing a cancer biomarker to clinical application, Cancer Res 1:52(9Suppl):2711s-2718s (1992).

Tomblyn et al., Guidelines for preventing infectious complications among hematopoietic cell transplantation recipients: A global perspective, Biol Blood Marrow Trans (2009) vol. 15:1143-1238.

Umeshita et al.: "Determination of the Presence of Interleukin-6 in Bile After Orthotropic Liver Transplantation," Annals of Surgery, vol. 223, No. 2, 204-211. 1996.

Vaes et al., Comprehensive microarray analysis of bone morphogenetic protein 2-induced osteoblast differentiation resulting in the identification of novel markers for bone development, J Bone Miner Res 17(12):2106-18 (2002).

Vaidya, et al., Biomarkers of acute kidney injury, Annual Review of Pharmacology and Toxicology, Annual Review Inc., vol. 48, pp. 463-493, Feb. 1, 2008.

Van Niel et al., Exosomes: a common pathway for a specialized function, J Biochem 140(1):13-21 (2006).

Van't Veer et al., Enabling personalized cancer medicine through analysis of gene-expression patterns, Nature 452(7187):564-70 (2008).

(56) References Cited

OTHER PUBLICATIONS

Vollenhofer-Schrumpf et al., A simple nucleic acid hybridization/latex agglutination assay for the rapid detection of polymerase chain reaction amplicons, J Microbiol Methods (2007) vol. 68(3):568-576.

Waikar et al., Diagnosis, Epidemiology and Outcomes of Acute Kidney Injury, Clinical Journal of the American Society of Nephrology, vol. 3, No. 3, pp. 844-861, Feb. 20, 2008.

Wakabayashi, Therapeutic Research, 2001, vol. 22, No. 11, p. 2433-2437.

Warlé et al.: "Early Differentiation Between Rejection and Infection in Liver Transplant Patients by Serum and Biliary Cytokine Patterns," Transplantation, vol. 75, 146-151, No. 1, Jan. 15, 2003.

Wellmann et al., Detection of differentially expressed genes in lymphomas using cDNA arrays: identification of clustering as a new diagnostic marker for anaplastic large-cell lymphomas, Blood (2000) vol. 96(2):398-404.

Whitehead et al., Variation in tissue-specific gene expression among natural populations, Genome Biol 6(2):R13 (2005).

Wu et al., Detection of PCR amplicons from bacterial pathogens using microsphere agglutination, J Microbiol Meth (2004) vol. 56:395-400.

Xu et al., Gene expression in peripheral blood differs after cardioembolic compared with large-vessel atherosclerotic stroke: biomarkers for the etiology of ischemic stroke, JCBFM (2008) vol. 28:1320-1328.

Yuan Y, et al., Urinary candidate biomarker discovery in a rat unilateral ureteral obstruction model. Sci. Rep., Mar. 20, 2015.

Zefon International. Glass Fiber Filters, Jan. 14, 2010 (printed from internet Oct. 7, 2011) <http://web.archive.org/web/20100114112921/http://www.zefon.com/store/glass-fiber-filters/>].

Zheng et al., Urinary Podocyte-Associated mRNA profile in Various Stages of Diabetic Nephropathy, PLOS one (2011) vol. 6(5):1-7.

Zhou et al., "Acute Kidney Injury Biomarkers—Needs, Present Status, and Future Promise," Nephrol Self Assess Program. Mar. 2006; 5(2):63-71.

Zhou et al., Exosomal Fetuin-A identified by proteomics: A novel urinary biomarker for detecting acute kidney injury, Kidney International, Nature Publishing Group, vol. 70, No. 10, Nov. 1, 2006, pp. 1847-1857.

Zhou et al., Urinary exosomal transcription factors, a new class of biomarkers for renal disease, Kidney Intl (2008) vol. 74(5):613-621.

Zucker et al., Immature platelet fraction as a predictor of platelet recovery following hematopoietic progenitor cell transplantation, Lab Hematol (2006) vol. 12:125-130.

* cited by examiner

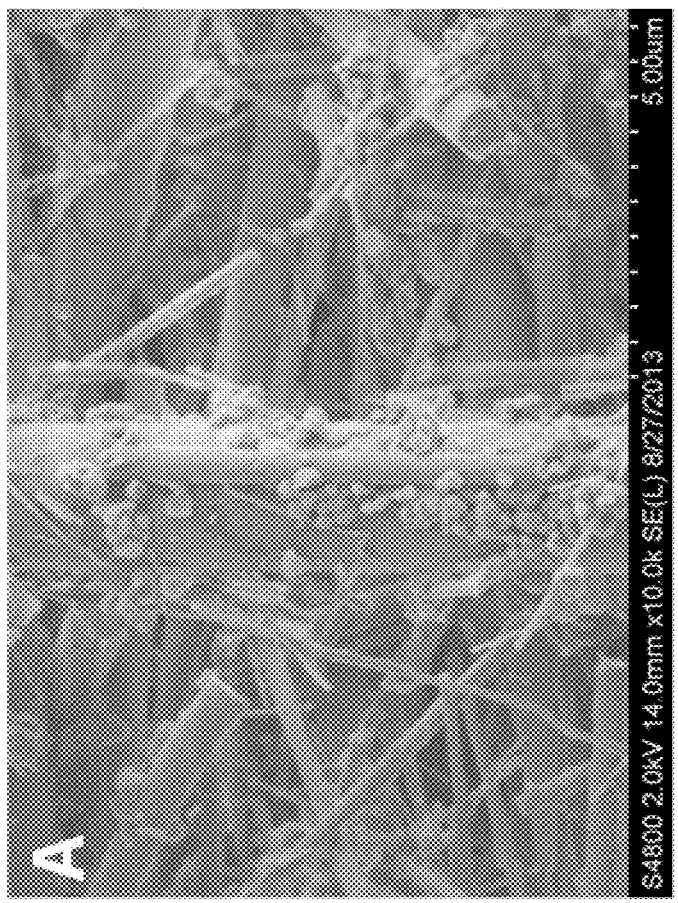
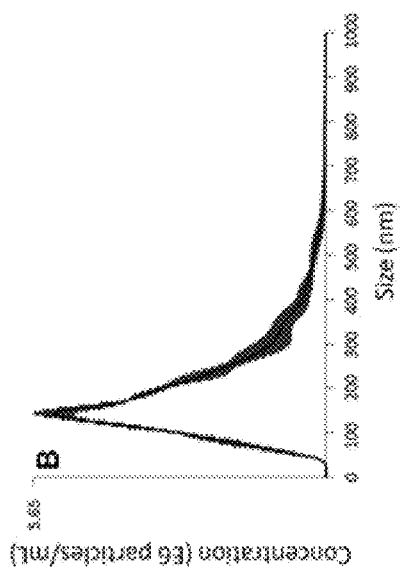
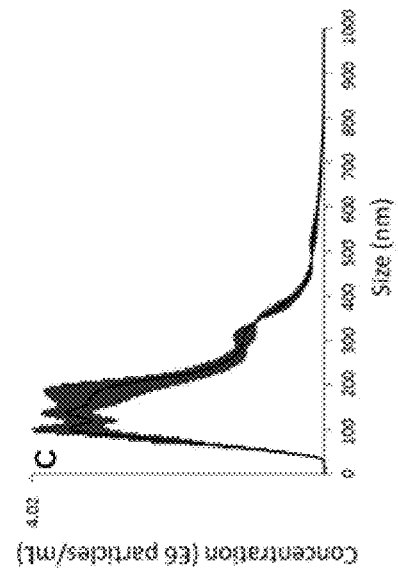
FIGURE 2A
FIGURE 2B
FIGURE 2C

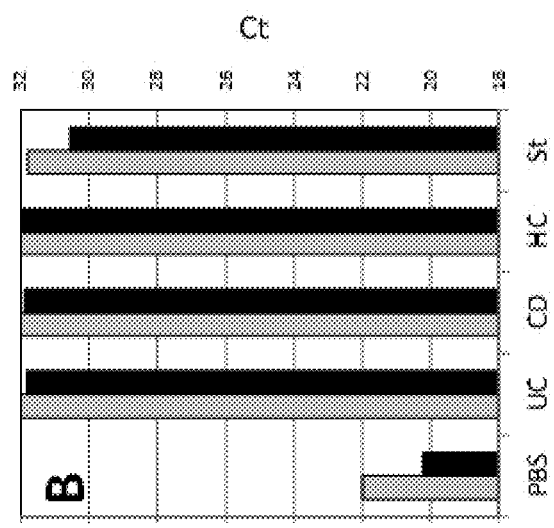
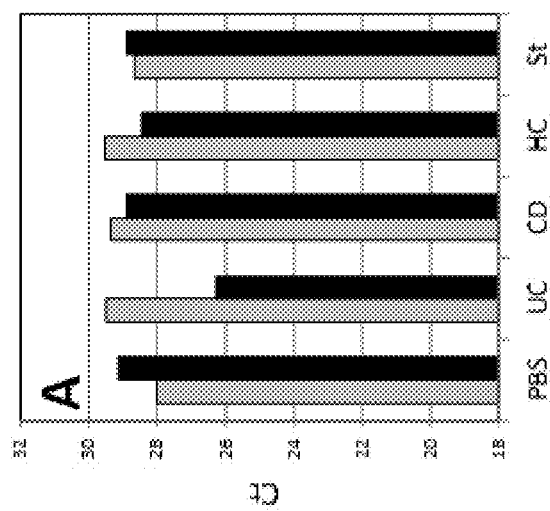
FIGURE 3A
FIGURE 3B

SEQUENCE LISTING

<160> NUMBER OF SEQ ID NOS: 112

<210> SEQ ID NO 1
<211> LENGTH: 18
<212> TYPE: DNA
<213> ORGANISM: Homo sapiens

<400> SEQUENCE: 1
cctggcaccc agcacaat                                                 18

<210> SEQ ID NO 2
<211> LENGTH: 20
<212> TYPE: DNA
<213> ORGANISM: Homo sapiens

<400> SEQUENCE: 2
gccgatccac acggagtact                                               20

<210> SEQ ID NO 3
<211> LENGTH: 20
<212> TYPE: DNA
<213> ORGANISM: Homo sapiens

<400> SEQUENCE: 3
cccactcctc cacctttgac                                               20

<210> SEQ ID NO 4
<211> LENGTH: 24
<212> TYPE: DNA
<213> ORGANISM: Homo sapiens

<400> SEQUENCE: 4
cataccagga aatgagcttg acaa                                          24

<210> SEQ ID NO 5
<211> LENGTH: 22
<212> TYPE: DNA
<213> ORGANISM: Homo sapiens

<400> SEQUENCE: 5
gcgggacatt tgtcatgtac tc                                            22

```
<210> SEQ ID NO 6
<211> LENGTH: 23
<212> TYPE: DNA
<213> ORGANISM: Homo sapiens

<400> SEQUENCE: 6
gatgtgggtg taggtgtgtg tca                                              23

<210> SEQ ID NO 7
<211> LENGTH: 21
<212> TYPE: DNA
<213> ORGANISM: Homo sapiens

<400> SEQUENCE: 7
gccttgagaa cgcctacaac a                                                21

<210> SEQ ID NO 8
<211> LENGTH: 22
<212> TYPE: DNA
<213> ORGANISM: Homo sapiens

<400> SEQUENCE: 8
gagctctgtg ccagagtcaa ca                                               22

<210> SEQ ID NO 9
<211> LENGTH: 19
<212> TYPE: DNA
<213> ORGANISM: Homo sapiens

<400> SEQUENCE: 9 tcccccggt atgagattg                                                    19

<210> SEQ ID NO 10
<211> LENGTH: 19
<212> TYPE: DNA
<213> ORGANISM: Homo sapiens

<400> SEQUENCE: 10
gcctgcagtg cccattatg                                                   19

<210> SEQ ID NO 11
<211> LENGTH: 23
<212> TYPE: DNA
<213> ORGANISM: Homo sapiens

<400> SEQUENCE: 11
cagttgttgc tggaattgtt gtg                                              23

<210> SEQ ID NO 12
<211> LENGTH: 25
<212> TYPE: DNA
<213> ORGANISM: Homo sapiens

<400> SEQUENCE: 12
catctcaccc atctcccttta tctca                                           25

<210> SEQ ID NO 13
<211> LENGTH: 24
<212> TYPE: DNA
<213> ORGANISM: Homo sapiens

<400> SEQUENCE: 13
ctgggatgca gaacatgagt attc                                             24
```

<210> SEQ ID NO 14
<211> LENGTH: 19
<212> TYPE: DNA
<213> ORGANISM: Homo sapiens

<400> SEQUENCE: 14
gcttgtgagg cccccatag                                                   19

<210> SEQ ID NO 15
<211> LENGTH: 20
<212> TYPE: DNA
<213> ORGANISM: Homo sapiens

<400> SEQUENCE: 15
ccttgccgca aagtgtgtaa                                                  20

<210> SEQ ID NO 16
<211> LENGTH: 22
<212> TYPE: DNA
<213> ORGANISM: Homo sapiens

<400> SEQUENCE: 16
tgaaggagtc acccctaaat gc                                               22

<210> SEQ ID NO 17
<211> LENGTH: 20
<212> TYPE: DNA
<213> ORGANISM: Homo sapiens

<400> SEQUENCE: 17
agtgcagtgg cacgatctca                                                  20

<210> SEQ ID NO 18
<211> LENGTH: 19
<212> TYPE: DNA
<213> ORGANISM: Homo sapiens

<400> SEQUENCE: 18
aaattagccg ggcgttgtg                                                   19

<210> SEQ ID NO 19
<211> LENGTH: 23
<212> TYPE: DNA
<213> ORGANISM: Homo sapiens

<400> SEQUENCE: 19
cggatggtag cagtctaggg att                                              23

<210> SEQ ID NO 20
<211> LENGTH: 22
<212> TYPE: DNA
<213> ORGANISM: Homo sapiens

<400> SEQUENCE: 20
ggaatgtccc atacccaaag aa                                               22

<210> SEQ ID NO 21
<211> LENGTH: 20
<212> TYPE: DNA
<213> ORGANISM: Homo sapiens

<400> SEQUENCE: 21
ccccagcacg gtgattagtc                                                  20

<210> SEQ ID NO 22
<211> LENGTH: 24
<212> TYPE: DNA
<213> ORGANISM: Homo sapiens

<400> SEQUENCE: 22
cagagcagtc aatctgtgtt gtga                                    24

<210> SEQ ID NO 23
<211> LENGTH: 20
<212> TYPE: DNA
<213> ORGANISM: Homo sapiens

<400> SEQUENCE: 23
tgcaaggctg acgataagga                                         20

<210> SEQ ID NO 24
<211> LENGTH: 26
<212> TYPE: DNA
<213> ORGANISM: Homo sapiens

<400> SEQUENCE: 24
gtaggctgag atgcttttaa atgtga                                  26

<210> SEQ ID NO 25
<211> LENGTH: 26
<212> TYPE: DNA
<213> ORGANISM: Homo sapiens

<400> SEQUENCE: 25
acagaggatt cattgttttc aacaat                                  26

<210> SEQ ID NO 26
<211> LENGTH: 22
<212> TYPE: DNA
<213> ORGANISM: Homo sapiens

<400> SEQUENCE: 26
acagtatgtg ccagcaggaa ga                                      22

<210> SEQ ID NO 27
<211> LENGTH: 27
<212> TYPE: DNA
<213> ORGANISM: Homo sapiens

<400> SEQUENCE: 27
gaactaaagg gatctgaaac aacattc                                 27

<210> SEQ ID NO 28
<211> LENGTH: 24
<212> TYPE: DNA
<213> ORGANISM: Homo sapiens

<400> SEQUENCE: 28
tgttgagatg atgctttgac aaaa                                    24

<210> SEQ ID NO 29
<211> LENGTH: 20
<212> TYPE: DNA
<213> ORGANISM: Homo sapiens

<400> SEQUENCE: 29

```
cacaggcaca agcagctgat                                              20

<210> SEQ ID NO 30
<211> LENGTH: 23
<212> TYPE: DNA
<213> ORGANISM: Homo sapiens

<400> SEQUENCE: 30
ccttcacagg acaggaattc aag                                          23

<210> SEQ ID NO 31
<211> LENGTH: 21
<212> TYPE: DNA
<213> ORGANISM: Homo sapiens

<400> SEQUENCE: 31
catgaactct gtccccatcc a                                            21

<210> SEQ ID NO 32
<211> LENGTH: 18
<212> TYPE: DNA
<213> ORGANISM: Homo sapiens

<400> SEQUENCE: 32
tccagccgga aggagttg                                                18

<210> SEQ ID NO 33
<211> LENGTH: 19
<212> TYPE: DNA
<213> ORGANISM: Homo sapiens

<400> SEQUENCE: 33
ccaaggctgg gcactcagt                                               19

<210> SEQ ID NO 34
<211> LENGTH: 23
<212> TYPE: DNA
<213> ORGANISM: Homo sapiens

<400> SEQUENCE: 34
gatgccaaga ctccagtcct aaa                                          23

<210> SEQ ID NO 35
<211> LENGTH: 22
<212> TYPE: DNA
<213> ORGANISM: Homo sapiens

<400> SEQUENCE: 35
cgaaggctcc aaagaagaca gt                                           22

<210> SEQ ID NO 36
<211> LENGTH: 20
<212> TYPE: DNA
<213> ORGANISM: Homo sapiens

<400> SEQUENCE: 36
cagggcaatg atcccaaagt                                              20

<210> SEQ ID NO 37
<211> LENGTH: 23
<212> TYPE: DNA
<213> ORGANISM: Homo sapiens

<400> SEQUENCE: 37
```

```
tgcgaagtag gtagcaactg gtt                                            23
```

<210> SEQ ID NO 38
<211> LENGTH: 22
<212> TYPE: DNA
<213> ORGANISM: Homo sapiens

<400> SEQUENCE: 38

```
ccattagctt gtccccttct tg                                             22
```

<210> SEQ ID NO 39
<211> LENGTH: 20
<212> TYPE: DNA
<213> ORGANISM: Homo sapiens

<400> SEQUENCE: 39

```
caatgtgcca ggctcttcct                                                20
```

<210> SEQ ID NO 40
<211> LENGTH: 22
<212> TYPE: DNA
<213> ORGANISM: Homo sapiens

<400> SEQUENCE: 40

```
tcacactcct cagctcctgg ta                                             22
```

<210> SEQ ID NO 41
<211> LENGTH: 20
<212> TYPE: DNA
<213> ORGANISM: Homo sapiens

<400> SEQUENCE: 41

```
gcggtggctt cctgatacaa                                                20
```

<210> SEQ ID NO 42
<211> LENGTH: 23
<212> TYPE: DNA
<213> ORGANISM: Homo sapiens

<400> SEQUENCE: 42

```
ccaaggtgac atttatggag ctt                                            23
```

<210> SEQ ID NO 43
<211> LENGTH: 19
<212> TYPE: DNA
<213> ORGANISM: Homo sapiens

<400> SEQUENCE: 43

```
actgcctggg ttccaatcc                                                 19
```

<210> SEQ ID NO 44
<211> LENGTH: 25
<212> TYPE: DNA
<213> ORGANISM: Homo sapiens

<400> SEQUENCE: 44

```
tgtttaagga gggtaatttg ctcaa                                          25
```

<210> SEQ ID NO 45
<211> LENGTH: 21
<212> TYPE: DNA
<213> ORGANISM: Homo sapiens

```
<400> SEQUENCE: 45
ccaggctcaa ggaaaaacat g                                              21

<210> SEQ ID NO 46
<211> LENGTH: 23
<212> TYPE: DNA
<213> ORGANISM: Homo sapiens

<400> SEQUENCE: 46
ctggtagatg caggttccat agc                                            23

<210> SEQ ID NO 47
<211> LENGTH: 25
<212> TYPE: DNA
<213> ORGANISM: Homo sapiens

<400> SEQUENCE: 47
gaagagtgag tggtgcaagt atgaa                                          25

<210> SEQ ID NO 48
<211> LENGTH: 23
<212> TYPE: DNA
<213> ORGANISM: Homo sapiens

<400> SEQUENCE: 48
atggcagcat cattgttctc atc                                            23

<210> SEQ ID NO 49
<211> LENGTH: 23
<212> TYPE: DNA
<213> ORGANISM: Homo sapiens

<400> SEQUENCE: 49
ggagaccatc aaggaagaca tga                                            23

<210> SEQ ID NO 50
<211> LENGTH: 20
<212> TYPE: DNA
<213> ORGANISM: Homo sapiens

<400> SEQUENCE: 50
gctttgcgtt ggacattcaa                                                20

<210> SEQ ID NO 51
<211> LENGTH: 20
<212> TYPE: DNA
<213> ORGANISM: Homo sapiens

<400> SEQUENCE: 51
cccccagagc tggttgttaa                                                20

<210> SEQ ID NO 52
<211> LENGTH: 23
<212> TYPE: DNA
<213> ORGANISM: Homo sapiens

<400> SEQUENCE: 52
ctggagtgtg cagagatgac aca                                            23

<210> SEQ ID NO 53
<211> LENGTH: 24
<212> TYPE: DNA
<213> ORGANISM: Homo sapiens
```

<400> SEQUENCE: 53
gccatgagtg agtttgacat cttc                                          24

<210> SEQ ID NO 54
<211> LENGTH: 29
<212> TYPE: DNA
<213> ORGANISM: Homo sapiens

<400> SEQUENCE: 54
gattttggag acctctaatt tatgtccta                                     29

<210> SEQ ID NO 55
<211> LENGTH: 19
<212> TYPE: DNA
<213> ORGANISM: Homo sapiens

<400> SEQUENCE: 55
cactgaggtc cgggtgaca                                                19

<210> SEQ ID NO 56
<211> LENGTH: 21
<212> TYPE: DNA
<213> ORGANISM: Homo sapiens

<400> SEQUENCE: 56
gtaggttgcc gcacagactt c                                             21

<210> SEQ ID NO 57
<211> LENGTH: 24
<212> TYPE: DNA
<213> ORGANISM: Homo sapiens

<400> SEQUENCE: 57
tccaagagag aggagaagct tttc                                          24

<210> SEQ ID NO 58
<211> LENGTH: 24
<212> TYPE: DNA
<213> ORGANISM: Homo sapiens

<400> SEQUENCE: 58
gctgtatggt tttcctcagg atct                                          24

<210> SEQ ID NO 59
<211> LENGTH: 26
<212> TYPE: DNA
<213> ORGANISM: Homo sapiens

<400> SEQUENCE: 59
agacaccaga agaagtaact cgaaca                                        26

<210> SEQ ID NO 60
<211> LENGTH: 19
<212> TYPE: DNA
<213> ORGANISM: Homo sapiens

<400> SEQUENCE: 60
tcccgagcaa gtccgaaac                                                19

<210> SEQ ID NO 61
<211> LENGTH: 24
<212> TYPE: DNA

<213> ORGANISM: Homo sapiens

<400> SEQUENCE: 61
ctgctgaggc tcaagttaaa agtg                24

<210> SEQ ID NO 62
<211> LENGTH: 21
<212> TYPE: DNA
<213> ORGANISM: Homo sapiens

<400> SEQUENCE: 62
tgaggtatcg ccaggaattg t                21

<210> SEQ ID NO 63
<211> LENGTH: 20
<212> TYPE: DNA
<213> ORGANISM: Homo sapiens

<400> SEQUENCE: 63
gcccatcact ttggcaaaga                20

<210> SEQ ID NO 64
<211> LENGTH: 22
<212> TYPE: DNA
<213> ORGANISM: Homo sapiens

<400> SEQUENCE: 64
ccagccacca ctttctgata gg                22

<210> SEQ ID NO 65
<211> LENGTH: 19
<212> TYPE: DNA
<213> ORGANISM: Homo sapiens

<400> SEQUENCE: 65
aaatgccaca cggctctca                19

<210> SEQ ID NO 66
<211> LENGTH: 21
<212> TYPE: DNA
<213> ORGANISM: Homo sapiens

<400> SEQUENCE: 66
gggtgctgtg cttctgtgaa c                21

<210> SEQ ID NO 67
<211> LENGTH: 23
<212> TYPE: DNA
<213> ORGANISM: Homo sapiens

<400> SEQUENCE: 67
ccgagagaac gagggctact att                23

<210> SEQ ID NO 68
<211> LENGTH: 22
<212> TYPE: DNA
<213> ORGANISM: Homo sapiens

<400> SEQUENCE: 68
gcacgaagtg gctgaagtac at                22

<210> SEQ ID NO 69
<211> LENGTH: 20

```
<212> TYPE: DNA
<213> ORGANISM: Homo sapiens

<400> SEQUENCE: 69
cagggaaagg ccagtgtgaa                                         20

<210> SEQ ID NO 70
<211> LENGTH: 22
<212> TYPE: DNA
<213> ORGANISM: Homo sapiens

<400> SEQUENCE: 70
accacgtgtt gtcttgctga at                                      22

<210> SEQ ID NO 71
<211> LENGTH: 21
<212> TYPE: DNA
<213> ORGANISM: Homo sapiens

<400> SEQUENCE: 71
aagctccctg aagcaaagga a                                       21

<210> SEQ ID NO 72
<211> LENGTH: 23
<212> TYPE: DNA
<213> ORGANISM: Homo sapiens

<400> SEQUENCE: 72
gcaggaccat tgacagaatg ttc                                     23

<210> SEQ ID NO 73
<211> LENGTH: 19
<212> TYPE: DNA
<213> ORGANISM: Homo sapiens

<400> SEQUENCE: 73
tgctgctgct caccatcct                                          19

<210> SEQ ID NO 74
<211> LENGTH: 19
<212> TYPE: DNA
<213> ORGANISM: Homo sapiens

<400> SEQUENCE: 74
ccggttccgc ttgaagaag                                          19

<210> SEQ ID NO 75
<211> LENGTH: 24
<212> TYPE: DNA
<213> ORGANISM: Homo sapiens

<400> SEQUENCE: 75
tcatcactgg tcttttggag tttg                                    24

<210> SEQ ID NO 76
<211> LENGTH: 20
<212> TYPE: DNA
<213> ORGANISM: Homo sapiens

<400> SEQUENCE: 76
tctgcacagc tctggcttgt                                         20

<210> SEQ ID NO 77
```

-continued

```
<211> LENGTH: 27
<212> TYPE: DNA
<213> ORGANISM: Homo sapiens

<400> SEQUENCE: 77
tgctaaagaa cttagatgtc agtgcat                                    27

<210> SEQ ID NO 78
<211> LENGTH: 23
<212> TYPE: DNA
<213> ORGANISM: Homo sapiens

<400> SEQUENCE: 78
tggtccactc tcaatcactc tca                                        23

<210> SEQ ID NO 79
<211> LENGTH: 28
<212> TYPE: DNA
<213> ORGANISM: Homo sapiens

<400> SEQUENCE: 79
gatacacaga ccgtattctt catcctaa                                   28

<210> SEQ ID NO 80
<211> LENGTH: 26
<212> TYPE: DNA
<213> ORGANISM: Homo sapiens

<400> SEQUENCE: 80
tgaaagatga tagcattgat gtcaca                                     26

<210> SEQ ID NO 81
<211> LENGTH: 22
<212> TYPE: DNA
<213> ORGANISM: Homo sapiens

<400> SEQUENCE: 81
aagctggaaa tgaagccaaa gt                                         22

<210> SEQ ID NO 82
<211> LENGTH: 20
<212> TYPE: DNA
<213> ORGANISM: Homo sapiens

<400> SEQUENCE: 82
acacgctctt ggtggtgatg                                            20

<210> SEQ ID NO 83
<211> LENGTH: 21
<212> TYPE: DNA
<213> ORGANISM: Homo sapiens

<400> SEQUENCE: 83
ggattccgct tattccttgg t                                          21

<210> SEQ ID NO 84
<211> LENGTH: 23
<212> TYPE: DNA
<213> ORGANISM: Homo sapiens

<400> SEQUENCE: 84
tgcgaaccca gctgttataa tct                                        23
```

```
<210> SEQ ID NO 85
<211> LENGTH: 20
<212> TYPE: DNA
<213> ORGANISM: Homo sapiens

<400> SEQUENCE: 85
cccagctgag caaccattgt                                              20

<210> SEQ ID NO 86
<211> LENGTH: 23
<212> TYPE: DNA
<213> ORGANISM: Homo sapiens

<400> SEQUENCE: 86
gaccagggag aatagaacca tga                                          23

<210> SEQ ID NO 87
<211> LENGTH: 23
<212> TYPE: DNA
<213> ORGANISM: Homo sapiens

<400> SEQUENCE: 87
aaagctgaca caaggaagat gga                                          23

<210> SEQ ID NO 88
<211> LENGTH: 25
<212> TYPE: DNA
<213> ORGANISM: Homo sapiens

<400> SEQUENCE: 88
tcaggaggat cacaatgatg actac                                        25

<210> SEQ ID NO 89
<211> LENGTH: 24
<212> TYPE: DNA
<213> ORGANISM: Homo sapiens

<400> SEQUENCE: 89
ttgtactgta tgccttcagc attg                                         24

<210> SEQ ID NO 90
<211> LENGTH: 24
<212> TYPE: DNA
<213> ORGANISM: Homo sapiens

<400> SEQUENCE: 90
tcggctgata aagcaaaata tttg                                         24

<210> SEQ ID NO 91
<211> LENGTH: 22
<212> TYPE: DNA
<213> ORGANISM: Homo sapiens

<400> SEQUENCE: 91
ggatcacagc tgctttctgt tg                                           22

<210> SEQ ID NO 92
<211> LENGTH: 24
<212> TYPE: DNA
<213> ORGANISM: Homo sapiens

<400> SEQUENCE: 92
cgaccgtgat acctttaatg acaa                                         24
```

<210> SEQ ID NO 93
<211> LENGTH: 22
<212> TYPE: DNA
<213> ORGANISM: Homo sapiens

<400> SEQUENCE: 93
ttgccagctc aaaagaaaac aa                                              22

<210> SEQ ID NO 94
<211> LENGTH: 21
<212> TYPE: DNA
<213> ORGANISM: Homo sapiens

<400> SEQUENCE: 94
accaacaggg taggcagaac a                                               21

<210> SEQ ID NO 95
<211> LENGTH: 19
<212> TYPE: DNA
<213> ORGANISM: Homo sapiens

<400> SEQUENCE: 95
ctgtgaggaa gcccaagca                                                  19

<210> SEQ ID NO 96
<211> LENGTH: 24
<212> TYPE: DNA
<213> ORGANISM: Homo sapiens

<400> SEQUENCE: 96
cagaatcacc tgaaggcttc ttct                                            24

<210> SEQ ID NO 97
<211> LENGTH: 21
<212> TYPE: DNA
<213> ORGANISM: Homo sapiens

<400> SEQUENCE: 97
cggaaggcaa gatcagatcc t                                               21

<210> SEQ ID NO 98
<211> LENGTH: 19
<212> TYPE: DNA
<213> ORGANISM: Homo sapiens

<400> SEQUENCE: 98
ccctggtgtc ctccatgct                                                  19

<210> SEQ ID NO 99
<211> LENGTH: 21
<212> TYPE: DNA
<213> ORGANISM: Homo sapiens

<400> SEQUENCE: 99
ggccaagcct aaccgctata a                                               21

<210> SEQ ID NO 100
<211> LENGTH: 25
<212> TYPE: DNA
<213> ORGANISM: Homo sapiens

<400> SEQUENCE: 100
cttctgaaag acagctgaca agaga                                           25

<210> SEQ ID NO 101
<211> LENGTH: 22
<212> TYPE: DNA
<213> ORGANISM: Homo sapiens

<400> SEQUENCE: 101
ctgagcttcg aggagttcat ca                                    22

<210> SEQ ID NO 102
<211> LENGTH: 19
<212> TYPE: DNA
<213> ORGANISM: Homo sapiens

<400> SEQUENCE: 102
cgtcaccctc gtgcatctt                                        19

<210> SEQ ID NO 103
<211> LENGTH: 24
<212> TYPE: DNA
<213> ORGANISM: Homo sapiens

<400> SEQUENCE: 103
gctaagagat tcgccttaaa tgct                                  24

<210> SEQ ID NO 104
<211> LENGTH: 20
<212> TYPE: DNA
<213> ORGANISM: Homo sapiens

<400> SEQUENCE: 104
cttggtgccc tccagtgagt                                       20

<210> SEQ ID NO 105
<211> LENGTH: 20
<212> TYPE: DNA
<213> ORGANISM: Bovine

<400> SEQUENCE: 105
ggcatgaagc atctcgatga                                       20

<210> SEQ ID NO 106
<211> LENGTH: 24
<212> TYPE: DNA
<213> ORGANISM: Bovine

<400> SEQUENCE: 106
cagcttatca cagtgcagct cact                                  24

<210> SEQ ID NO 107
<211> LENGTH: 21
<212> TYPE: DNA
<213> ORGANISM: Bovine

<400> SEQUENCE: 107
aggttgtctc ctgcgacttc a                                     21

<210> SEQ ID NO 108
<211> LENGTH: 19
<212> TYPE: DNA
<213> ORGANISM: Bovine

<400> SEQUENCE: 108

```
gtggtcgttg agggcaatg                                             19

<210> SEQ ID NO 109
<211> LENGTH: 22
<212> TYPE: DNA
<213> ORGANISM: Rat

<400> SEQUENCE: 109
tctgtgtgga ttggtggctc ta                                         22

<210> SEQ ID NO 110
<211> LENGTH: 21
<212> TYPE: DNA
<213> ORGANISM: Rat

<400> SEQUENCE: 110
ctgcttgctg atccacatct g                                          21

<210> SEQ ID NO 111
<211> LENGTH: 23
<212> TYPE: DNA
<213> ORGANISM: Rat

<400> SEQUENCE: 111
accaggttgt ctcctgtgac ttc                                        23

<210> SEQ ID NO 112
<211> LENGTH: 24
<212> TYPE: DNA
<213> ORGANISM: Rat

<400> SEQUENCE: 112
caggaaatga gcttcacaaa gttg                                       24
```

EXOSOMES AND MICROVESICLES IN INTESTINAL LUMINAL FLUIDS AND STOOL AND USE OF SAME FOR THE ASSESSMENT OF INFLAMMATORY BOWEL DISEASE

RELATED CASES

This application claims the benefit of U.S. Provisional Application Ser. No. 62/075,683, filed on Nov. 5, 2014, the entire disclosure of which is incorporated by reference herein.

REFERENCE TO SEQUENCE LISTING

A Sequence Listing submitted as an ASCII text file via EFS-Web is hereby incorporated by reference in accordance with 35 U.S.C. § 1.52(e). The name of the ASCII text file for the Sequence Listing is 21977440_1.TXT, the date of creation of the ASCII text file is Nov. 3, 2015, and the size of the ASCII text file is 16.5 KB.

BACKGROUND

Field

The present disclosure relates to the methods for using intestinal luminal fluid (ILF) to collect exosomes and/or microvesicles (collectively referred to as EMV) in order to detect inflammatory bowel diseases (IBD). Several embodiments relate to the treatment and/or ongoing monitoring of treatment of IBD.

Description of Related Art

IBD are a collection of diseases that result in an inflammation of the gastrointestinal (GI) tract, and the two most common IBD are ulcerative colitis (UC) and Crohn's disease (CD). UC is a disease that causes long-lasting inflammation and sores in the innermost lining of the colon and rectum. CD can develop anywhere in the digestive tract and can penetrate into the deep layers of the affected tissue. The diseases are similar, however, in that both can cause abdominal pain, severe diarrhea, fatigue and weight loss. It is estimated that as many as 1.4 million persons in the United States suffer from these diseases with an overall health care cost of more than $1.7 billion. Each year in the United States, IBD accounts for more than 700,000 physician visits, 100,000 hospitalizations, and disability in 119,000 patients.

SUMMARY

EMV can be isolated from various biological fluids such as urine, blood, and saliva. EMV can protect the RNA enclosed therein from degradation by nucleases, allowing EMV to be used as potential non-invasive sources of biomarkers. In several embodiments, the detected biomarker can be used to develop an appropriate treatment regimen. In some embodiments, however, the treatment may be taking no further action (e.g., not instituting a treatment). In some embodiments, expression of a biomarker is detected by a method comprising liberating RNA from the isolated membrane particles, cells, exosomes, exosome-like vesicles, and/or microvesicles, contacting the liberated RNA with a reverse transcriptase to generate complementary DNA (cDNA), and contacting the cDNA with sense and antisense primers that are specific for the biomarker of the disease or condition to be treated and a DNA polymerase in order to generate amplified DNA. In several embodiments the methods are computerized (e.g., one or more of the RNA isolation, cDNA generation, or amplification are controlled, in whole or in part, by a computer). In several embodiments, the detection of the biomarker is real time. Additionally, in several embodiments, the method includes informing a medical professional of the test results, wherein the informing is performed by computer or other form of network communication. In several such embodiments, the computers (or tablets, smartphones, etc.) involved in transmitting or receiving of the expression information comprise a dynamic graphical user interface that provides the physician with therapeutic options for treating the subject, when appropriate and allows the physician to filter or otherwise refine the information provided based on therapeutic preferences derived from characteristics specific to the subject.

In several embodiments, provided herein are methods for diagnosing and treating an IBD in a human subject comprising passing an intraluminal fluid sample comprising vesicles of the human subject through a vesicle-capture material, thereby generating a vesicle sample; performing a nucleic acid-based detection assay to detect mRNA expression level of one or more genes in said vesicle sample, wherein said one or more genes is selected from the group consisting of epithelial cell adhesion molecule (EPCAM), mucin 2 (MUC2), trefoil factor 1 (TFF1), defensin alpha 3 (DEFA3), lymphocyte common antigen (CD45), transforming growth factor beta 1 (TGFB1), and S100 calcium binding protein A9 (S100A9); determining that said vesicle sample expresses said one or more genes at a level significantly different from the expression level of the respective gene in a vesicle sample of a healthy human control subject not suffering from said IBD, thereby diagnosing the human subject as having IBD; providing a recommendation for the administration of an effective amount of an anti-inflammatory medication to the human subject expressing the one or more genes at a level significantly different from the expression level of the respective genes in a vesicle sample of a healthy human control subject not suffering from said IBD, thereby treating IBD in the human subject. In some embodiments, the intraluminal fluid sample is a blood sample, a urine sample, a saliva sample or an intestinal fluid sample. In several embodiments, the vesicle-capture material is a filter comprising glass fiber. In some embodiments, captured EMV are lysed on or in the vescle-capture material. In several embodiments, the IBD can be ulcerative colitis or Crohn's disease.

In several embodiments, provided herein are methods for developing a treatment plan for an individual suffering from symptoms of an IBD comprising capturing vesicles from a stool or an ILF of the individual, quantifying an expression level of one or more messenger RNA (mRNA) in the captured vesicles, comparing the expression level of the one or more mRNA from the captured vesicles of the individual to the expression level of the one or more mRNA in captured vesicles of a pool of subjects not suffering from IBD, identifying whether the individual is suffering from an IBD based on the result of the comparison, and developing a treatment plan for the individual based on the result of the comparison, wherein the individual is identified as suffering from an IBD if the expression level of the one or more mRNAs from the captured vesicles of the individual is statistically significantly different from the expression level of the one or more mRNAs from the captured vesicles of the pool of individuals not suffering from an IBD, and wherein the individual is identified as not suffering from an IBD if the expression level of one or more mRNAs from the captured vesicles of the individual is not statistically significantly different from the expression level of the one or more mRNAs from the captured vesicles of the pool of individuals not suffering from an IBD.

In some embodiments, a method of treating a subject suffering from an IBD comprises: ordering a test of an ILF or stool obtained from the subject, obtaining the results of the test, and treating the subject when the test results indicate that the subject is suffering from an IBD. In some embodiments, the test comprises the steps of isolating one or more of membrane particles, cells, exosomes, exosome-like vesicles, and/or microvesicles from the ILF or stool of the subject, liberating RNA from the isolated membrane particles, cells, exosomes, exosome-like vesicles, and microvesicles, contacting the liberated RNA with a reverse transcriptase to generate complementary DNA (cDNA), contacting the cDNA with sense and antisense primers that are specific for one or more markers of IBD and with a DNA polymerase in order to generate amplified DNA, and detecting the amount of expression of the markers of IBD. As above, certain aspects of the methods are optionally computerized. Also, in several embodiments, the amount of expression may result in a determination that no treatment is to be undertaken at that time. Thus, in several embodiments, the methods disclosed herein also reduce unnecessary medical expenses and reduce the likelihood of adverse effects from a treatment that is not needed at that time. In several embodiments, detecting the amount of expression of the markers of IBD comprises quantifying an expression level of at least two genes in said vesicle sample, wherein said at least two genes is selected from the group consisting of epithelial cell adhesion molecule (EPCAM), mucin 2 (MUC2), trefoil factor 1 (TFF1), defensin alpha 3 (DEFA3), lymphocyte common antigen (CD45), transforming growth factor beta 1 (TGFB1), and S100 calcium binding protein A9 (S100A9). In several embodiments, the method further comprises determining said subject as having said IBD when said expression level of each of said at least two genes is significantly different from the expression level of the respective gene in a vesicle sample of a healthy human control subject not suffering from said IBD, thereby diagnosing said subject as having IBD; and administering an effective amount of an IBD medication to the human subject having said IBD, wherein said IBD medication is selected from the group consisting of an aminosalicylate, a corticosteroid, an immunosuppressor, and a TNF-alpha inhibitor, thereby treating said IBD in said human subject.

In several embodiments, provided herein are methods for determining the efficacy of a treatment plan administered to an individual suffering from one or more symptoms of an IBD comprising obtaining a first sample of a stool or an ILF of the individual prior to an administration of a treatment for the IBD, obtaining a second sample of a stool or an ILF of the individual after administration of the treatment for the IBD, capturing vesicles from the first and second samples, quantifying an expression level of one or more marker mRNAs from the captured vesicles of the first and second samples, identifying whether the treatment plan is effective by comparing the expression level of the one or more marker mRNAs in the first sample to the expression level of the one or more marker mRNAs in the second sample, wherein the treatment plan is identified as effective when the one or more marker mRNAs in the first sample is statistically different from the expression level of the one or more marker mRNAs in the second sample. In some embodiments, the treatment plan is identified as effective if the expression level of the one or more marker mRNAs in the second sample is not statistically significantly different from the expression level of the one or more marker mRNAs from the captured vesicles of a pool of individuals not suffering from the IBD, while the expression level of the one or more marker mRNAs in the first sample is statistically significantly different from the expression level of the one or more marker mRNAs from the captured vesicles of a pool of individuals not suffering from the IBD. In several embodiments, quantifying an expression level of one or more mRNAs in said first and second vesicle samples comprises quantifying an expression level of at least one gene in said vesicle sample, wherein said at least one gene is selected from the group consisting of epithelial cell adhesion molecule (EPCAM), mucin 2 (MUC2), trefoil factor 1 (TFF1), defensin alpha 3 (DEFA3), lymphocyte common antigen (CD45), transforming growth factor beta 1 (TGFB1), and S100 calcium binding protein A9 (S100A9).

In several embodiments, provided herein are methods of processing a stool or an ILF sample of an individual suffering from an IBD comprising capturing vesicles from the stool or ILF sample by passing a liquid comprising at least a portion of the sample through a vesicle-capture device comprising a filter, positioning the filter of the vesicle-capture device in proximity to a substrate that includes immobilized oligo(dT), lysing the vesicles while the vesicles are on or in the filter to release one or more marker mRNAs from the vesicle-capture device and onto the substrate, hybridizing the one or more marker mRNAs released from the vesicle-capture device with the immobilized oligo(dT) on the substrate, synthesizing on the substrate one or more complementary DNA (cDNA) from the one or more marker mRNAs that hybridize with the immobilized oligo(dT) on the substrate, and quantifying by quantitative reverse transcription polymerase chain reaction (RT-qPCR) analysis the expression level of one or more of the marker mRNAs.

In some embodiments, the EMV are isolated from the ILF or stool sample using one or more types of physical force. In some embodiments, a syringe or syringe-like device is used to isolate the material (e.g., via suction or, alternatively, via positive pressure). In other embodiments, centrifugation, shaking, air pressure, or liquid pressure are used. Combinations may also be used, in several embodiments. In some embodiments, EMV are isolated from the ILF or stool by filtering the sample. In some embodiments, filtering the collected sample will trap one or more of membrane particles, exosomes, exosome-like vesicles, and microvesicles on a filter. In some embodiments, the filter comprises material to capture components that are about 1.6 microns or greater in diameter. In several embodiments, a plurality of filters are used to capture vesicles within a particularly preferred range of sizes (e.g., diameters). For example, in several embodiments, filters are used to capture vesicles having a diameter of from about 0.2 microns to about 1.6 microns in diameter, including about 0.2 microns to about 0.4 microns, about 0.4 microns to about 0.6 microns, about 0.6 microns to about 0.8 microns, about 0.8 microns to about 1.0 microns, about 1.0 microns to about 1.2 microns, about 1.2 to about 1.4 microns, about 1.4 microns to about 1.6 microns (and any size in between those listed). In other embodiments, the vesicle-capture material captures exosomes ranging in size from about 0.5 microns to about 1.0 microns.

In some embodiments, the filter (or filters) comprises glass-like material, non-glass-like material, or a combination thereof. In some embodiments, wherein the vesicle-capture material comprises glass-like materials, the vesicle-capture material has a structure that is disordered or "amorphous" at the atomic scale, like plastic or glass. Glass-like materials include, but are not limited to glass beads or fibers, silica beads (or other configuration), nitrocellulose, nylon, polyvinylidene fluoride (PVDF) or other similar polymers, metal or nano-metal fibers, polystyrene, ethylene vinyl acetate or other co-polymers, natural fibers (e.g., silk), alginate fiber, or combinations thereof. In certain embodiments, the vesicle-capture material optionally comprises a plurality of layers of vesicle-capture material. In other embodiments, the vesicle-capture material further comprises nitrocellulose.

In some aspects, the vesicles are captured from a stool or ILF of the individual by passing a liquid sample comprising the stool or ILF through a vesicle-capture device. In some embodiments, the vesicle-capture device includes a filter. In some aspects, the vesicle-capture device includes a filter containing glass fiber. In some aspects the vesicle-capture device includes a loading reservoir reversibly coupled to a tip that houses a vesicle-capture material, the loading reservoir having a volume capacity that is two to twenty times larger than the volume capacity of the tip. In several aspects, the removable tip of the vesicle-capture device is adapted to rest on a frame that holds the removable tip in close proximity to a substrate. In some embodiments, the substrate includes immobilized oligo(dT). In some embodiments, the substrate includes immobilized nucleotide primers. In some embodiments the substrate includes a gene-chip. In some aspects, the frame forms a substantially liquid tight seal with the substrate.

In some embodiments, a filter device is used to isolate biological components of interest. In some embodiments, the device comprises: a first body having an inlet, an outlet, and an interior volume between the inlet and the outlet; a second body having an inlet, an outlet, an interior volume between the inlet and the outlet, a filter material positioned within the interior volume of the second body and in fluid communication with the first body; and a receiving vessel having an inlet, a closed end opposite the inlet and interior cavity. In some embodiments, the first body and the second body are reversibly connected by an interaction of the inlet of the second body with the outlet of the first body. In some embodiments, the interior cavity of the receiving vessel is dimensioned to reversibly enclose both the first and the second body and to receive the collected sample after it is passed from the interior volume of the first body, through the filter material, through the interior cavity of the second body and out of the outlet of the second body. In some embodiments, the isolating step comprises placing at least a portion of the collected sample in such a device, and applying a force to the device to cause the collected sample to pass through the device to the receiving vessel and capture the biological component of interest. In some embodiments, applying the force comprises centrifugation of the device. In other embodiments, applying the force comprises application of positive pressure to the device. In other embodiments, applying the force comprises application of vacuum pressure to the device. Non-limiting examples of such filter devices are disclosed in PCT Publication WO 2014/182330 and PCT Publication WO 2015/050891, hereby incorporated by reference herein.

In some embodiments, the collected sample is passed through multiple filters to isolate the biological component of interest. In other embodiments, isolating biological components comprises diluting the collected sample. In other embodiments, centrifugation may be used to isolate the biological components of interest. In some embodiments, multiple isolation techniques may be employed (e.g., combinations of filtration selection and/or density centrifugation). In some embodiments, the collected sample is separated into one or more samples after the isolating step.

In some embodiments, RNA is liberated from the biological component of interest for measurement. In some embodiments, liberating the RNA from the biological component of interest comprises lysing the membrane particles, exosomes, exosome-like vesicles, and/or microvesicles with a lysis buffer. In other embodiments, centrifugation may be employed. In some embodiments, the liberating is performed while the membrane particles, exosomes, exosome-like vesicles, microvesicles and/or other components of interest are immobilized on a filter. In some embodiments, the membrane particles, exosomes, exosome-like vesicles, microvesicles and/or other components of interest are isolated or otherwise separated from other components of the collected sample (and/or from one another—e.g., vesicles separated from exosomes).

In several embodiments, the liberated RNA comprises one or more marker mRNAs that encodes a marker selected from the group consisting of epithelial cell adhesion molecule (EPCAM), mucin 2 (MUC2), trefoil factor 1 (TFF1), defensin alpha 3 (DEFA3), lymphocyte common antigen (CD45), transforming growth factor beta 1 (TGFB1), and S100 calcium binding protein A9 (S100A9). In several aspects, the ILF is selected from the group consisting of blood, urine, saliva, and intestinal fluid.

In some embodiments, the RNA liberated from the biological components of interest comprises poly(A)+RNA. According to various embodiments, various methods to quantify RNA are used, including Northern blot analysis, RNAse protection assay, PCR, RT-PCR, real-time RT-PCR, other quantitative PCR techniques, RNA sequencing, nucleic acid sequence-based amplification, branched-DNA amplification, mass spectrometry, CHIP-sequencing, DNA or RNA microarray analysis and/or other hybridization microarrays. In some of these embodiments or alternative embodiments, after amplified DNA is generated, it is exposed to a probe complementary to a portion of a biomarker of interest.

In some embodiments, a computerized method is used to complete one or more of the steps. In some embodiments, the computerized method comprises exposing a reaction mixture comprising isolated RNA and/or prepared cDNA, a polymerase and gene-specific primers to a thermal cycle. In some embodiments, the thermal cycle is generated by a computer configured to control the temperature time, and cycle number to which the reaction mixture is exposed. In other embodiments, the computer controls only the time or only the temperature for the reaction mixture and an individual controls on or more additional variables. In some embodiments, a computer is used that is configured to receive data from the detecting step and to implement a program that detects the number of thermal cycles required for the biomarker to reach a pre-defined amplification threshold in order to identify whether a subject is suffering from a intestinal disease or condition. In still additional embodiments, the entire testing and detection process is automated.

For example, in some embodiments, RNA is isolated by a fully automated method, e.g., methods controlled by a computer processor and associated automated machinery. In one embodiment a biological sample, such as ILF or stool, is collected and loaded into a receiving vessel that is placed into a sample processing unit. A user enters information into a data input receiver, such information related to sample identity, the sample quantity, and/or specific patient characteristics. In several embodiments, the user employs a graphical user interface to enter the data. In other embodiments, the data input is automated (e.g., input by bar code, QR code, or other graphical identifier). The user can then implement an RNA isolation protocol, for which the computer is configured to access an algorithm and perform associated functions to process the sample in order to isolate biological components, such as vesicles, and subsequently processed the vesicles to liberate RNA. In further embodiments, the computer implemented program can quantify the amount of RNA isolated and/or evaluate and purity. In such embodiments, should the quantity and/or purity surpass a minimum threshold, the RNA can be further processed, in an automated fashion, to generate cDNA. cDNA can then be generated, such as for example, binding of a poly-A RNA tail to an oligo dT molecule and subsequent extension using an RNA polymerase. In other embodiments, if the quantity and/or purity fail to surpass a minimum threshold, the computer implemented program can prompt a user to provide additional biological sample(s).

Depending on the embodiment, the cDNA can be divided into individual subsamples, some being stored for later analysis and some being analyzed immediately. Analysis, in some embodiments comprises mixing a known quantity of the cDNA with a salt-based buffer, a DNA polymerase, and at least one gene specific primer to generate a reaction mixture. The cDNA can then be amplified using a predetermined thermal cycle program that the computer system is configured to implement. This thermal cycle, could optionally be controlled manually as well. After amplification (e.g., real-time PCR), the computer system can assess the number of cycles required for a gene of interest (e.g. a marker of intestinal disease or condition) to surpass a particular threshold of expression. A data analysis processor can then use this assessment to calculate the amount of the gene of interest present in the original sample, and by comparison either to a different patient sample, a known control, or a combination thereof, expression level of the gene of interest can be calculated. A data output processor can provide this information, either electronically in another acceptable format, to a test facility and/or directly to a medical care provider. Based on this determination, the medical care provider can then determine if and how to treat a particular patient based on determining the presence of an IBD. In several embodiments, the expression data is generated in real time, and optionally conveyed to the medical care provider (or other recipient) in real time.

In several embodiments, a fully or partially automated method enables faster sample processing and analysis than manual testing methods. In certain embodiments, machines or testing devices may be portable and/or mobile such that a physician or laboratory technician may complete testing outside of a normal hospital or laboratory setting. In some embodiments, a portable assay device may be compatible with a portable device comprising a computer such as a cell phone or lap top that can be used to input the assay parameters to the assay device and/or receive the raw results of a completed test from the assay device for further processing. In some embodiments, a patient or other user may be able to use an assay device via a computer interface without the assistance of a laboratory technician or doctor. In these cases, the patient would have the option of performing the test "at-home." In certain of these embodiments, a computer with specialized software or programming may guide a patient to properly place a sample in the assay device and input data and information relating to the sample in the computer before ordering the tests to run. After all the tests have been completed, the computer software may automatically calculate the test results based on the raw data received from the assay device. The computer may calculate additional data by processing the results and, in some embodiments, by comparing the results to control information from a stored library of data or other sources via the internet or other means that supply the computer with additional information. The computer may then display an output to the patient (and/or the medical care provider, and/or a test facility) based on those results.

In some embodiments, a medical professional may be in need of genetic testing in order to diagnose, monitor and/or treat a patient. Thus, in several embodiments, a medical professional may order a test and use the results in making a diagnosis or treatment plan for a patient. For example, in some embodiments a medical professional may collect a sample from a patient or have the patient otherwise provide a sample (or samples) for testing. The medical professional may then send the sample to a laboratory or other third party capable of processing and testing the sample. Alternatively, the medical professional may perform some or all of the processing and testing of the sample himself/herself (e.g., in house). Testing may provide quantitative and/or qualitative information about the sample, including data related to the presence of an IBD. Once this information is collected, in some embodiments the information may be compared to control information (e.g., to a baseline or normal population) to determine whether the test results demonstrate a difference between the patient's sample and the control. After the information is compared and analyzed, it is returned to the medical professional for additional analysis. Alternatively, the raw data collected from the tests may be returned to the medical professional so that the medical professional or other hospital staff can perform any applicable comparisons and analyses. Based on the results of the tests and the medical professional's analysis, the medical professional may decide how to treat or diagnose the patient (or optionally refrain from treating).

In some embodiments, expression of a biomarker is compared to expression of the biomarker in a control sample. In some embodiments, the control sample is based on the expression of the biomarker in a healthy individual, or an individual who is not suffering from an IBD. In other embodiments, the control sample is based on an average or control RNA expression profile generated based on the average biomarker expression of multiple healthy individuals. In other embodiments, the control sample is based on the expression of the biomarker in an individual who is suffering from an IBD. In other embodiments, the control sample is generated by a computer that has received data for subjects whose biomarker expression levels have been analyzed. In some embodiments, multiple samples are taken from the same individual at different times over the course of days, weeks, months, or years. In these embodiments, the earlier data collected may be used to generate a control sample to compare to the later data. In addition, these multiple samples can be used to track whether (and how) mRNA expression changes in a patient over time.

In some embodiments, an mRNA expression profile is generated for one or more mRNA associated with an IBD or any other biomarkers. In some embodiments, the mRNA expression profile may be generated to include a comparison of the expression of a biomarker in an individual to the expression of the biomarker in a control sample, where the control sample is generated by any of the methods described above or through alternative means that similarly provide a data reference point. In some embodiments, an mRNA expression profile may be based on mRNA data collected from the individual patient alone, where expression data was collected on either one or multiple occasions.

In some embodiments, greater expression of a biomarker indicates a subject is suffering from an IBD. In other embodiments, reduced expression of a biomarker indicates a subject is suffering from an IBD. Depending on the marker, and the embodiment, increases or decreases in expression may be statistically significant (e.g., p-values less than 0.05 by art-accepted statistical analysis methods). In some embodiments, expression is compared against a control value or expression profile to determine whether a subject is suffering from an IBD compared to the control. In some embodiments, expression indicating IBD or lack thereof is corroborated with a histological evaluation of a biopsy of a cell or tissue population of interest, or with a colonoscopy evaluation of the subject.

In some embodiments, the IBD is treated with oral, systemically administered or locally administered medication. Medications are not limited to a compound that is generally considered of medicinal purpose (e.g., a prescribed or over the counter drug) but may also include any dietary or nutrition supplement(s). Therefore, for example, a vitamin, a mineral, an herb or other botanical, an amino acid, a dietary substance for use by a subject to supplement the diet by increasing the total dietary intake (e.g., enzymes or tissues from organs or glands), or a concentrate, metabolite, constituent or extract can also be applicable to the methods disclosed herein. In other embodiments, the IBD is treated with surgery or further inspection of the subject, such as with ultrasound. In some embodiments, the subject is treated using intestinal rescission surgery. In some embodiments, the subject is treated by administering anti-inflammatory agents (e.g., an aminosalicylate, a corticosteroid), an immunosuppressor (e.g., cyclosporine, mercaptopurine, azathiopurine), a biologic (e.g., TNF-alpha inhibitor), or combinations thereof.

BRIEF DESCRIPTION OF THE FIGURES

FIG. 2A depicts a SEM image of EMV captured on a collection filter.

FIG. 2B shows size-distribution plots of EMV isolated from ILF.

FIG. 2C shows size-distribution plots of EMV isolated from stool.

FIG. 3A shows stability of bovine EMV mRNA when suspended in different solutions.

FIG. 3B shows naked rat mRNA is degraded when suspended in different solutions.

DETAILED DESCRIPTION

Figure 1A:
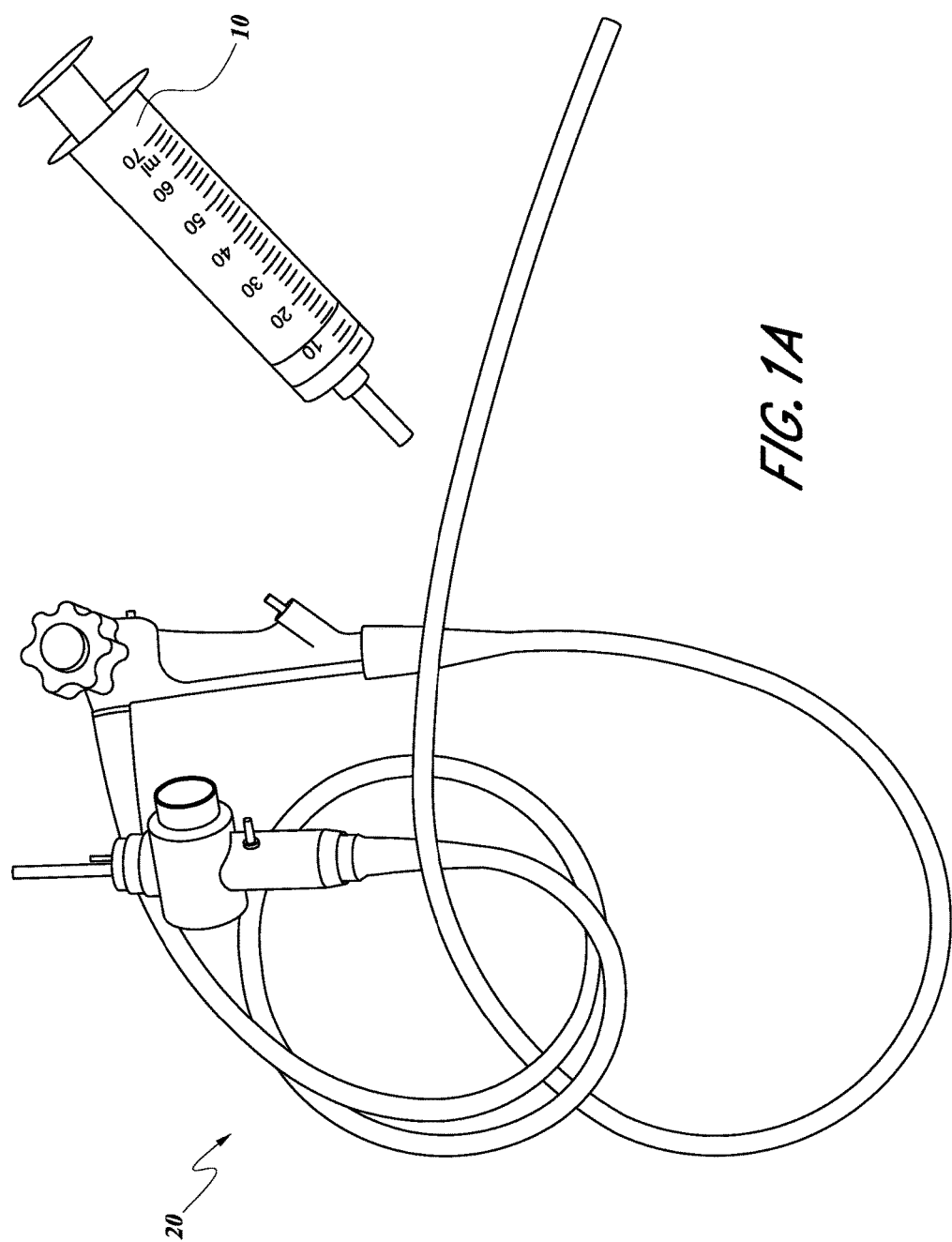
FIG. 1A depicts an embodiment of a colonoscopy catheter and a syringe that can be used for aspiration of ILF.

In several embodiments described herein, methods are provided for using a stool or ILF sample from an individual suffering from one or more symptoms of IBD to develop a treatment plan for the individual. IBDs are characterized by a general range of signs and symptoms that are commonly shared by other conditions. These symptoms include abdominal pain, diarrhea, fever, weight loss and fatigue. Physicians typically collect and evaluate a combination of information to make the diagnosis. The various exams and tests to make the diagnosis may include a stool exam, complete blood count, barium X-ray, sigmoidoscopy, colonoscopy, or upper endoscopy. However, there is currently no single test that can determine the diagnosis of UC or CD with certainty.

Thus, there exists a need for methods of identifying whether an individual is suffering from UC or CD, thereby allowing a medical professional to develop and administer treatment plans that are directed to the pathophysiology from which the individual is suffering. Moreover, methods that identify UC or CD would enable care-givers to monitor the efficacy of the treatment plans being administered to the individual.

Therefore, in several embodiments, methods are provided for the identification of individuals suffering from UC or CD. In certain embodiments, the methods are minimally-invasive, using EMV obtained from ILF such as saliva or urine, thereby reducing pain or discomfort to the individual and increasing patient compliance with the diagnostic method.

Recent studies have demonstrated that a variety of cells release EMV into nearby biological fluids, such as blood, urine, saliva, breast milk. During the exocytotic process, various proteins, mRNA, and miRNA are included in the EMV. Although naked mRNAs are instantly digested and become undetectable due to the presence of endogenous ribonucleases, mRNAs exist stably in EMV by encapsulation within the EMV membranes. Various mRNAs in EMV extracted from plasma and urine have been quantified by RT-qPCR. It is believed that stools and feces contain EMV, and that miRNA are found in such EMV. However, no prior reports disclose identification or detection of less abundant and/or unstable mRNA.

EMV are nm-sized particles that contain proteins and nucleic acids such as miRNA and mRNA that are representative of the cells from which the EMV are derived. For example, nucleic acids can be associated with one or more different types of membrane particles (ranging in size from 50-80 nm), exosomes (ranging in size from 50-100 nm), exosome-like vesicles (ranging in size from 20-50 nm), and microvesicles (ranging in size from 100-1000 nm). In several embodiments, these vesicles are isolated and/or concentrated, thereby preserving vesicle associated RNA even if there is a high RNAse extracellular environment. The RNAs within these particles have been shown to be functional and can confer specific activity to target cells.

Exosomes and microvesicles originating from the gastrointestinal tract can be isolated from samples from subjects having normal and diseased conditions. The miRNA and protein profiles from exosomes of subjects diagnosed with IBD are significantly different than those derived from non-IBD subjects. Thus, as described in several embodiments herein, exosomes and microvesicles and their contents can be used as diagnostic markers for screening, detecting and/or monitoring (or other treatment) of IBD.

The present disclosure relates to the use of ILF or stool EMV to detect IBD, and/or treat (or monitor ongoing treatment) of a subject with IBD. A variety of methods can be used, according to the embodiments disclosed herein, to efficiently capture and preserve vesicle associated RNA. In several embodiments, centrifugation on a density gradient to fractionate the non-cellular portion of the sample is performed. In some embodiments, density centrifugation is optionally followed by high speed centrifugation to cause vesicle sedimentation or pelleting. As such approaches may be time consuming and may require expensive and specialized equipment in several embodiments, low speed centrifugation can be employed to collect vesicles.

In several embodiments, filtration (alone or in combination with centrifugation) is used to capture vesicles of different sizes. In some embodiments, differential capture of vesicles is made based on the surface expression of protein markers. For example, a filter may be designed to be reactive to a specific surface marker (e.g., filter coupled to an antibody) or specific types of vesicles or vesicles of different origin. In several embodiments, the combination of filtration and centrifugation allows a higher yield or improved purity of vesicles.

In some embodiments, the markers are unique vesicle proteins or peptides. In some embodiments, the severity or identity of a particular IBD is associated with certain vesicle modifications which can be exploited to allow isolation of particular vesicles. Modification may include, but is not limited to addition of lipids, carbohydrates, and other molecules such as acylated, formylated, lipoylated, myristolylated, palmitoylated, alkylated, methylated, isoprenylated, prenylated, amidated, glycosylated, hydroxylated, iodinated, adenylated, phosphorylated, sulfated, and selenoylated, ubiquitinated. In some embodiments, the vesicle markers comprise non-proteins such as lipids, carbohydrates, nucleic acids, RNA, DNA, etc.

In several embodiments, the specific capture of vesicles based on their surface markers also enables a "dip stick" format where each different type of vesicle is captured by dipping probes coated with different capture molecules (e.g., antibodies with different specificities) into a patient sample.

In several embodiments, EMV from ILF were captured on an EMV filter collection tube device. In some embodiments the supernatant from a low speed spin can be the starting point for further isolation using conventional ultracentrifugation or can then be added to an exosome and microvesicle-capture filter device. In some embodiments, after application of the supernatant to the filter device, another low speed spin may be used to concentrate the particles onto the filter and remove the liquid. A lysis buffer may be added to the filter to release RNA. A low speed spin may be used to transfer the lysate from the filter device and in to the wells of an oligo(dT)-coated plate. The mRNA from the sample may be hybridized to the plate and the captured mRNA can be eluted and may be used for further downstream analysis. In several embodiments, after collection of the biological fluid containing membrane particles, cells, exosomes and microvesicles, molecular analysis of DNA, protein, membrane surface antigens, and miRNA can be performed in addition to mRNA analysis.

In some embodiments, EMV mRNA were released from the filter using a lysis buffer and isolated with an oligo(dT)-coupled plate. Depending on the embodiment, various epithelial-, immune/inflammatory-, blood cell-derived-, chemokine-, and miscellaneous mRNAs are evaluated (e.g., levels of expression are assessed, in some cases versus an appropriate control).

Thus, in several embodiments, the methods disclosed herein relate to the analysis of ILF for the presence of exosomes and/or microvesicles in order to identify potential biomarkers for the detection, diagnosis, screening or monitoring of IBD. ILF include, but are not limited to blood, urine, saliva, breast milk, intestinal fluid, and the like. Additionally or alternatively, stool samples can be used in some embodiments.

Samples of ILF can be collected by various means and at various times, depending on the embodiment. For example, in several embodiments, ILF is collected during colonoscopy or endoscopy. In certain embodiments, the ILF is collected from the intestine of the individual. In some embodiments, the ILF is collected from a portion of the gastrointestinal tract other than the intestine. In some embodiments, the ILF is a blood sample that is collected from the individual. The blood sample can be a whole blood sample. In several embodiments, the collected whole blood is heparinized upon collection. In several embodiments, the collected whole blood is stored at 4° C. until the whole blood is used for collecting EMV. In other embodiments, blood cells may be separated from the plasma or serum, with EMV being collected from either the plasma, serum, or blood cell fractions. In some embodiments, the ILF is collected from the individual before administration of an IBD treatment plan. In many embodiments, the ILF is collected from the individual at one or more times subsequent to initiating an IBD treatment plan.

In several embodiments, IBD alters the expression of one or more markers that are associated with inflammation or with the gastrointestinal tract. In several embodiments, expression of various markers are evaluated from the EMV collected from the ILF. For example, markers include, but are not limited to epithelial-related genes such as EPCAM, MUC2, and/or TFF1, leukocyte-derived inflammation-related genes such as DEFA3, CD45, TGFB1 and/or S100A9.

EPCAM is the gene of epithelial cell adhesion molecule, a transmembrane glycoprotein mediating $Ca^{2+}$-independent homotypic cell-cell adhesion in epithelia, and the level of EPCAM expression correlates with the proliferative activity of intestinal cells. Although EPCAM mRNA expression was not well characterized in IBD, the decreased levels of EPCAM found in ILF EMV (FIG. 4-5) suggest damage to epithelial cells. Weak adhesion of intestinal cells may enhance the communication between intestinal lumen and mucosa to activate the immune-inflammation response.

MUC2 is the gene of mucin 2, an oligomeric mucus/gel-forming protein prominent in the gut where it is secreted from goblet cells in the epithelial lining into the lumen of the intestine. TFF1 is the gene of Trefoil factor 1, a stable secretory proteins expressed in GI mucosa. Since both proteins are responsible for the protection of the mucosa, the decreased levels of MUC2 and TFF1 found in ILF EMV (FIG. 4-5) may correspond to the damage of epithelial cells in IBD.

Figure 4:
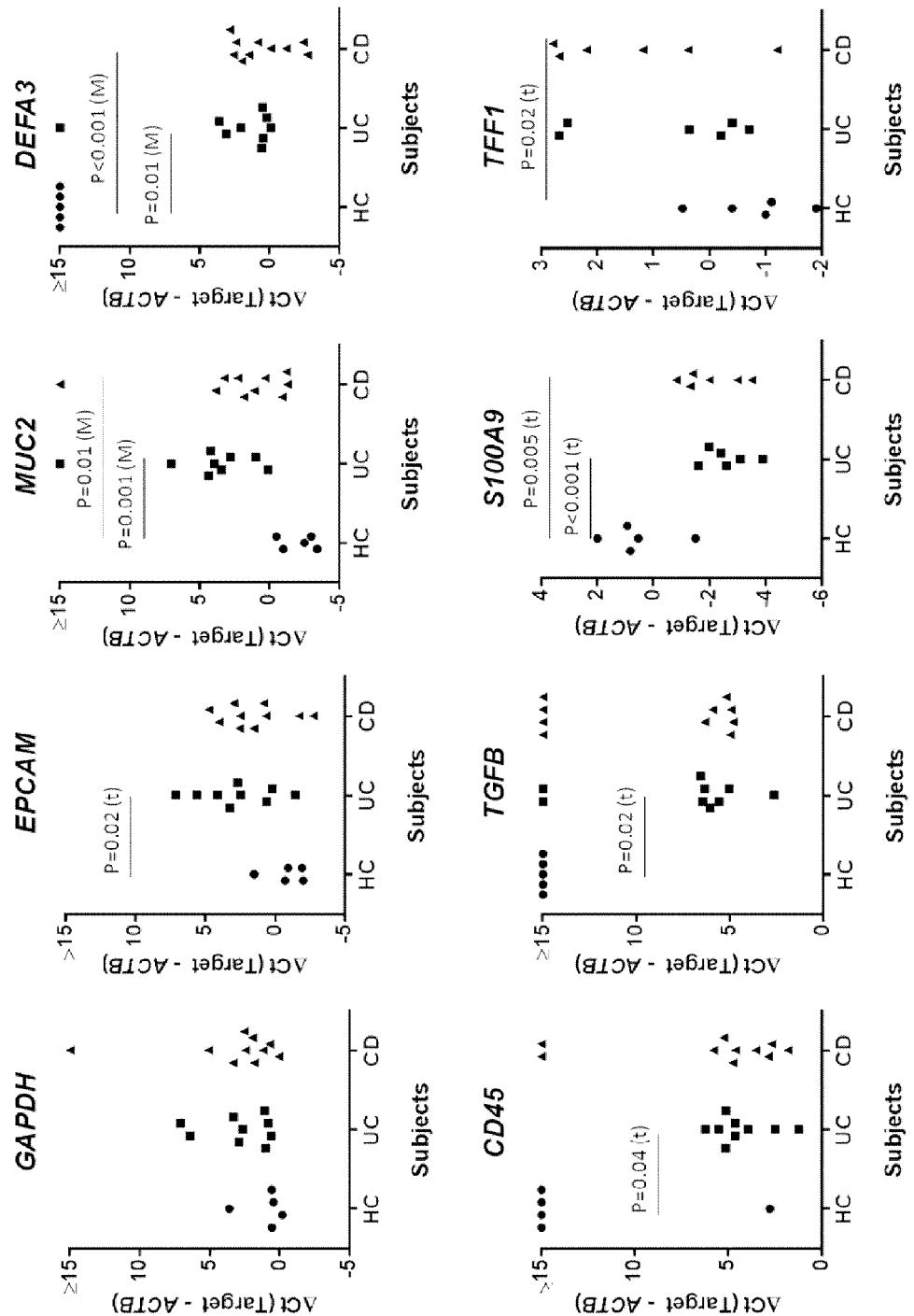
FIG. 4 shows mRNA expression levels in EMV isolated from ILF.

CD45 is the gene of leukocyte common antigen, not specific to any subtypes of leukocytes. In contrast, DEFA3 is the gene of a defensin 3, a family of microbicidal and cytotoxic peptides found mainly in neutrophils. The detection of this gene in ILF EMV indicates the presence of neutrophils in the intestine and their activation. DEFA3 was not detected in control subjects, whereas all except 1 IBD subjects showed this gene expression in ILF EMV (FIG. 4). Since neutrophil infiltration in the mucosa is one of the typical pathological findings of IBD, the detection of DEFA3 in ILF EMV may have a huge potential as a diagnostic biomarker of IBD.

TGFB1 is the gene of transforming growth factor β1. Since it acts as an anti-proliferative factor in normal epithelial cells, the elevation of this gene in ILF EMV may be associated with the decrease of EPCAM, MUC2, and TFF1 (FIG. 4). However, when the data of TGFB1 were compared with those of EPCAM, MUC2, and TFF1, $r^2$ values were 0.343, 0.134, and 0.086, respectively (data not shown). Thus, TGFB1 was not strongly associated with epithelial cell proliferation. TGFB1 also plays a role in regulation of the immune system by blocking the activation of lymphocytes and monocyte derived phagocytes via regulatory T cells (Treg). The elevation of TGFB1 in ILF EMV may indicate an activation of Treg in IBD, and may help to identify the appropriate patient population for Treg therapy.

S100A9 is known as migration inhibitory factor-related protein 14 (MRP-14) or calgranulin-B. Although it is involved in the regulation of a number of cellular processes such as cell cycle progression and differentiation, the role in IBD is not well characterized.

Methodology

Free extracellular RNA is quickly degraded by nucleases, making it a potentially poor diagnostic marker. As described above, some extracellular RNA is associated with particles or vesicles that can be found in various biological samples, such as intestinal fluid. This vesicle associated RNA, which includes mRNA, is protected from the degradation processes in the intestinal fluid. Microvesicles are shed from most cell types and consist of fragments of plasma membrane. Microvesicles contain RNA, mRNA, microRNA, and proteins and mirror the composition of the cell from which they are shed. Exosomes are small microvesicles secreted by a wide range of mammalian cells and are secreted under normal and pathological conditions. These vesicles contain certain proteins and RNA including mRNA and microRNA. Several embodiments evaluate nucleic acids such as small interfering RNA (siRNA), tRNA, and small activating RNA (saRNA), among others.

In several embodiments the RNA isolated from vesicles from the ILF of a patient is used as a template to make cDNA, for example through the use of a reverse transcriptase. In several embodiments, cDNA is amplified using the polymerase chain reaction (PCR). In other embodiments, amplification of nucleic acid and RNA may also be achieved by any suitable amplification technique such as nucleic acid based amplification (NASBA) or primer-dependent continuous amplification of nucleic acid, or ligase chain reaction. Other methods may also be used to quantify the nucleic acids, such as for example, including Northern blot analysis, RNAse protection assay, RNA sequencing, RT-PCR, real-time RT-PCR, nucleic acid sequence-based amplification, branched-DNA amplification, ELISA, mass spectrometry, CHIP-sequencing, and DNA or RNA microarray analysis.

In several embodiments, mRNA is quantified by a method entailing cDNA synthesis from mRNA and amplification of cDNA using PCR. In one preferred embodiment, a multi-well filterplate is washed with lysis buffer and wash buffer. A cDNA synthesis buffer is then added to the multi-well filterplate. The multi-well filterplate can be centrifuged. PCR primers are added to a PCR plate, and the cDNA is transferred from the multi-well filterplate to the PCR plate. The PCR plate is centrifuged, and real time PCR is commenced.

An additional embodiment comprises application of specific antisense primers during mRNA hybridization or during cDNA synthesis. It is preferable that the primers be added during mRNA hybridization, so that excess antisense primers may be removed before cDNA synthesis to avoid carryover effects. The oligo(dT) and the specific primer (NNNN) simultaneously prime cDNA synthesis at different locations on the poly-A RNA. The specific primer (NNNN) and oligo(dT) cause the formation of cDNA during amplification. Even when the specific primer-derived cDNA is removed from the GenePlate by heating each well, the amounts of specific cDNA obtained from the heat denaturing process (for example, using TaqMan quantitative PCR) is similar to the amount obtained from an un-heated negative control. This allows the heat denaturing process to be completely eliminated. Moreover, by adding multiple antisense primers for different targets, multiple genes can be amplified from the aliquot of cDNA, and oligo(dT)-derived cDNA in the GenePlate can be stored for future use.

Another additional embodiment involves a device for high-throughput quantification of mRNA from ILF or stool. The device includes a multi-well filterplate containing: multiple sample-delivery wells, an exosome-capturing filter (or filter directed to another biological component of interest) underneath the sample-delivery wells, and an mRNA capture zone under the filter, which contains oligo(dT)-immobilized in the wells of the mRNA capture zone. In order to increase the efficiency of exosome collection, several filtration membranes can be layered together.

In some embodiments, amplification comprises conducting real-time quantitative PCR (TaqMan) with exosome-derived RNA and control RNA. In some embodiments, a Taqman assay is employed. The 5' to 3' exonuclease activity of Taq polymerase is employed in a polymerase chain reaction product detection system to generate a specific detectable signal concomitantly with amplification. An oligonucleotide probe, nonextendable at the 3' end, labeled at the 5' end, and designed to hybridize within the target sequence, is introduced into the polymerase chain reaction assay. Annealing of the probe to one of the polymerase chain reaction product strands during the course of amplification generates a substrate suitable for exonuclease activity. During amplification, the 5' to 3' exonuclease activity of Taq polymerase degrades the probe into smaller fragments that can be differentiated from undegraded probe. In other embodiments, the method comprises: (a) providing to a PCR assay containing a sample, at least one labeled oligonucleotide containing a sequence complementary to a region of the target nucleic acid, wherein the labeled oligonucleotide anneals within the target nucleic acid sequence bounded by the oligonucleotide primers of step (b); (b) providing a set of oligonucleotide primers, wherein a first primer contains a sequence complementary to a region in one strand of the target nucleic acid sequence and primes the synthesis of a complementary DNA strand, and a second primer contains a sequence complementary to a region in a second strand of the target nucleic acid sequence and primes the synthesis of a complementary DNA strand; and wherein each oligonucleotide primer is selected to anneal to its complementary template upstream of any labeled oligonucleotide annealed to the same nucleic acid strand; (c) amplifying the target nucleic acid sequence employing a nucleic acid polymerase having 5' to 3' nuclease activity as a template dependent polymerizing agent under conditions which are permissive for PCR cycling steps of (i) annealing of primers and labeled oligonucleotide to a template nucleic acid sequence contained within the target region, and (ii) extending the primer, wherein said nucleic acid polymerase synthesizes a primer extension product while the 5' to 3' nuclease activity of the nucleic acid polymerase simultaneously releases labeled fragments from the annealed duplexes comprising labeled oligonucleotide and its complementary template nucleic acid sequences, thereby creating detectable labeled fragments; and (d) detecting and/or measuring the release of labeled fragments to determine the presence or absence of target sequence in the sample.

In alternative embodiments, a Taqman assay is employed that provides a reaction that results in the cleavage of single-stranded oligonucleotide probes labeled with a light-emitting label wherein the reaction is carried out in the presence of a DNA binding compound that interacts with the label to modify the light emission of the label. The method utilizes the change in light emission of the labeled probe that results from degradation of the probe. The methods are applicable in general to assays that utilize a reaction that results in cleavage of oligonucleotide probes, and in particular, to homogeneous amplification/detection assays where hybridized probe is cleaved concomitant with primer extension. A homogeneous amplification/detection assay is provided which allows the simultaneous detection of the accumulation of amplified target and the sequence-specific detection of the target sequence.

In alternative embodiments, real-time PCR formats may also be employed. One format employs an intercalating dye, such as SYBR Green. This dye provides a strong fluorescent signal on binding double-stranded DNA; this signal enables quantification of the amplified DNA. Although this format does not permit sequence-specific monitoring of amplification, it enables direct quantization of amplified DNA without any labeled probes. Other such fluorescent dyes that may also be employed are SYBR Gold, YO-PRO dyes and Yo Yo dyes.

Another real-time PCR format that may be employed uses reporter probes that hybridize to amplicons to generate a fluorescent signal. The hybridization events either separate the reporter and quencher moieties on the probes or bring them into closer proximity. The probes themselves are not degraded and the reporter fluorescent signal itself is not accumulated in the reaction. The accumulation of products during PCR is monitored by an increase in reporter fluorescent signal when probes hybridize to amplicons. Formats in this category include molecular beacons, dual-hybe probes, Sunrise or Amplifluor, and Scorpion real-time PCR assays.

Another real-time PCR format that may also be employed is the so-called "Policeman" system. In this system, the primer comprises a fluorescent moiety, such as FAM, and a quencher moiety which is capable of quenching fluorescence of the fluorescent moiety, such as TAMRA, which is covalently bound to at least one nucleotide base at the 3' end of the primer. At the 3' end, the primer has at least one mismatched base and thus does not complement the nucleic acid sample at that base or bases. The template nucleic acid sequence is amplified by PCR with a polymerase having 3'-5' exonuclease activity, such as the Pfu enzyme, to produce a PCR product. The mismatched base(s) bound to the quencher moiety are cleaved from the 3' end of the PCR product by 3'-5' exonuclease activity. The fluorescence that results when the mismatched base with the covalently bound quencher moiety is cleaved by the polymerase, thus removing the quenching effect on the fluorescent moiety, is detected and/or quantified at least one time point during PCR. Fluorescence above background indicates the presence of the synthesized nucleic acid sample.

Another additional embodiment involves a fully automated system for performing high throughput quantification of mRNA in ILF or stool, including: robots to apply ILF or stool samples, hypotonic buffer, and lysis buffer to the device; an automated vacuum aspirator and centrifuge, and automated PCR machinery.

In some embodiments, in order to more accurately quantify the amount of mRNA, quantification is calculated by comparing the amount of mRNA encoding a marker of IBD to a reference value. In some embodiments the reference value will be the amount of mRNA found in healthy non-diseased patients. In other embodiments, the reference value is the expression level of a house-keeping gene. In certain such embodiments, beta-actin, or other appropriate house-keeping gene is used as the reference value. Numerous other house-keeping genes that are well known in the art may also be used as a reference value. In other embodiments, a house keeping gene is used as a correction factor, such that the ultimate comparison is the expression level of marker from a diseased patient as compared to the same marker from a non-diseased (control) sample. In several embodiments, the house keeping gene is a tissue specific gene or marker, such as those discussed above. In still other embodiments, the reference value is zero, such that the quantification of the markers is represented by an absolute number. In several embodiments a ratio comparing the expression of one or more markers from a diseased patient to one or more other markers from a non-diseased person is made. In several embodiments, the comparison to the reference value is performed in real-time, such that it may be possible to make a determination about the sample at an early stage in the expression analysis. For example, if a sample is processed and compared to a reference value in real time, it may be determined that the expression of the marker exceeds the reference value after only a few amplification cycles, rather than requiring a full-length analysis. In several embodiments, this early comparison is particularly valuable, such as when a rapid diagnosis and treatment plan are required (e.g., to treat aggressive cancers or infections prior to possible development of sepsis).

In additional embodiments, the ability to determine the total efficiency of a given sample by using known amounts of spiked standard RNA results from embodiments being dose-independent and sequence-independent. The use of known amounts of control RNA allows PCR measurements to be converted into the quantity of target mRNAs in the original samples.

In certain embodiments, IBD is detected as a statistically significant upregulation or downregulation of expression of one or more marker mRNAs in EMV collected from a stool or ILF sample, with statistical significance being measured with standard statistical analyses with $p \leq 0.05$ representing a statistically significant change. In several embodiments, a significant increase in the expression of one or more marker mRNAs is an indication that the individual is suffering from an IBD. In several embodiments, a significant decrease in expression of one or more marker mRNAs is an indication that the individual is suffering from an IBD. In some embodiments, statistical significance is determined by comparing the expression of one or more marker mRNA in EMV obtained from a stool or ILF of an individual to the marker mRNA expression levels in a pool of individuals not suffering from IBD, where the mean and variance of the mRNA expression of the pool are determined by analyzing mRNA expression levels in EMV obtained from a stool or ILF of the individuals in the pool. In some embodiments, statistical significance is determined by comparing the expression of one or more marker mRNA in EMV obtained from a stool or ILF of an individual at a first time point to the expression of one or more marker mRNA in EMV obtained from a stool or ILF of an individual at a second time point. In some embodiments, the mean and variance of the mRNA expression of the individual is determined by analyzing samples in at least triplicate at each of the first and second time points.

Figure 5:
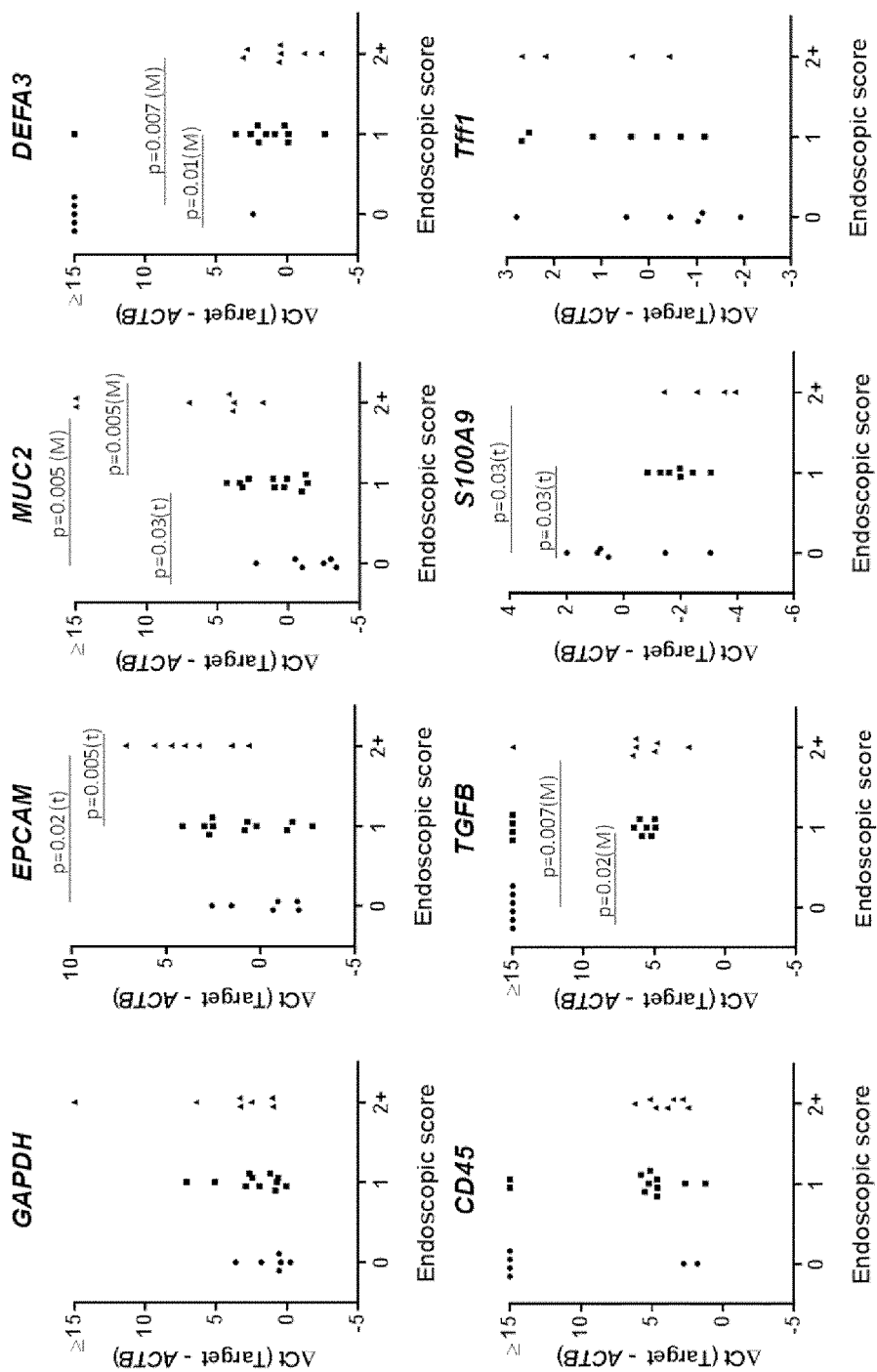
FIG. 5 shows correlation between endoscopic score and the levels of EMV mRNA in ILF.

In some embodiments, the results of EPCAM, MUC2, DEFA3, TGFB, and S100A9 were also correlated with the degree of endoscopic score (FIG. 5). Using multivariate discriminant analysis, mRNA data were capable of distinguishing HC, UC, and CD with 83.3% (HC and UC) and 75% (CD) predictability. In several embodiments, a stool sample contained EMV mRNAs. These data suggest that ILF and stool are rich source of EMV, and the quantification of function-specific mRNA in such EMV will be a valuable tool for the characterization of IBD.

In several embodiments, stool or ILF samples obtained from an individual can be combined with one or more agents that facilitate capture of EMV on a vesicle-capture device. For example, the EMV-containing stool or ILF samples can be combined with a buffer that alters the pH or salt concentration of the sample, thereby facilitating bonding of the EMV with a vesicle capture material (e.g., glass-fiber filter). Additionally or alternatively, the methods disclosed herein may include passing a buffer over a vesicle capture material after EMV have been retained therein to facilitate elution of the EMV from the vesicle capture material.

In certain embodiments, EMV are captured using a device that comprises a loading reservoir reversibly coupled to a tip that houses a vesicle-capture material, with the loading reservoir having a volume capacity that is two to twenty times larger than the volume capacity of the tip. In some embodiments, an EMV-containing sample is loaded into the loading reservoir and drawn through the vesicle-capture material by centrifugation or by applying a pressure differential across the vesicle capture material. In several aspects, the removable tip of the vesicle-capture device is adapted to rest on a frame that holds the removable tip in close proximity to a substrate. In some embodiments, the device comprises a sample multi-well plate that contains a plurality of sample-delivery wells, a EMV-capturing filter underneath the wells, and a substrate underneath the filter which contains immobilized oligo(dT). In some embodiments, the EMV-containing sample is drawn from the sample-delivery wells across the vesicle capture material by centrifugation of the multi-well plate. In certain embodiments, the device also contains a vacuum box adapted to receive the filter plate to create a seal between the plate and the box, such that when vacuum pressure is applied, the EMV-containing sample is drawn from the sample-delivery wells across the vesicle capture material, thereby capturing the EMV and allowing non-EMV components to be removed by washing the filters. In some embodiments, the EMV components are released from the filter by applying lysis buffer to the filter.

In some embodiments, the substrate includes immobilized oligo(dT). In some embodiments, the substrate includes immobilized nucleotide primers. In some embodiments the substrate includes a gene-chip. In some aspects, the frame or plate forms a substantially liquid tight seal with the substrate. In several embodiments, the method comprises loading the EMV-containing sample into the loading reservoir, drawing the sample across the vesicle-capture material, thereby trapping the EMV on or in the vesicle-capture material, detaching the tip from the loading reservoir, placing the tip into the frame, and releasing the EMV from the vesicle-capture material. In some embodiments, releasing the EMV comprises applying lysis buffer to the vesicle-capture material. Further detail regarding the composition of lysis buffers that may be used in several embodiments can be found in U.S. Pat. No. 8,101,344, filed Mar. 15, 2006, which is incorporated in its entirety by reference herein.

In several embodiments, cDNA is synthesized from oligo (dT)-immobilized mRNA. In certain embodiments, cDNA is then amplified using real time PCR with primers specifically designed for amplification of IBD-associated markers. Primers that are used in such embodiments are shown in Supplemental Table I. Further details about the PCR reactions used in some embodiments are also found in U.S. Pat. No. 8,101,344.

After the completion of a PCR reaction, the mRNA (as represented by the amount of PCR-amplified cDNA detected) for one or more IBD markers is quantified. In certain embodiments, quantification is calculated by comparing the amount of mRNA encoding one or more IBD markers to a reference value. In several embodiments, the reference value is expression level of a gene that is not induced in IBD, e.g., a house-keeping gene. In certain embodiments, beta-actin is used as the reference value. Numerous other house-keeping genes that are well known in the art may also be used as a reference value. In other embodiments, a house-keeping gene is used as a correction factor, such that the ultimate comparison is the induced or downregulated expression of one or more IBD markers as compared to the same marker from a pool of non-IBD (control) individuals. In still other embodiments, the reference value is zero, such that the quantification of one or more IBD markers is represented by an absolute number.

In several embodiments, the methods described herein are used to monitor an individual's responsiveness to ongoing IBD treatment. In some such embodiments, a first stool or ILF sample is obtained from the individual. In some embodiments, the first blood sample is obtained prior to the administration of any IBD treatment to the individual. In other embodiments, the individual has received treatment for IBD in the past, and will again in the future. In some embodiments, a second stool or ILF sample is obtained from the individual at a time after the taking of the first sample. In certain embodiments, this time is several hours, though in other embodiments, the time is several weeks, and in some embodiments up to several months. In other embodiments, additional samples are taken serially over the course of several months. In some embodiments, the samples are frozen until expression analysis, which is performed as described above.

Evaluation of expression levels of IBD responsive markers can thus be used to monitor the progress (e.g., efficiency) of an IBD treatment plan that is administered to the individual. In some embodiments, a significant difference in expression of one or more IBD responsive markers between the post-treatment sample and the pre-treatment sample indicates that the treatment therapy is effective. In other embodiments, a lack of a significant difference in expression of one or more IBD responsive markers between the post-treatment sample and the pre-treatment sample indicates that the treatment therapy is not effective.

In some embodiments, a kit is provided for extracting target components from ILF or stool samples. In some embodiments, a kit comprises a capture device and additional items useful to carry out methods disclosed herein. In some embodiments, a kit comprises one or more reagents selected from the group consisting of lysis buffers, chaotropic reagents, washing buffers, alcohol, detergent, or combinations thereof. In some embodiments, kit reagents are provided individually or in storage containers. In several embodiments, kit reagents are provided ready-to-use. In some embodiments, kit reagents are provided in the form of stock solutions that are diluted before use. In some embodiments, a kit comprises plastic parts (optionally sterilized or sterilizable) that are useful to carry out methods herein disclosed. In some embodiments, a kit comprises plastic parts selected from the group consisting of racks, centrifuge tubes, vacuum manifolds, and multi-well plates. Instructions for use are also provided, in several embodiments.

Implementation Mechanisms

According to some embodiments, the methods described herein can be implemented by one or more special-purpose computing devices. The special-purpose computing devices may be hard-wired to perform the techniques, or may include digital electronic devices such as one or more application-specific integrated circuits (ASICs) or field programmable gate arrays (FPGAs) that are persistently programmed to perform the techniques, or may include one or more general purpose hardware processors programmed to perform the techniques pursuant to program instructions in firmware, memory, other storage, or a combination. Such special-purpose computing devices may also combine custom hard-wired logic, ASICs, or FPGAs with custom programming to accomplish the techniques. The special-purpose computing devices may be desktop computer systems, server computer systems, portable computer systems, handheld devices, networking devices or any other device or combination of devices that incorporate hard-wired and/or program logic to implement the techniques.

Computing device(s) are generally controlled and coordinated by operating system software, such as iOS, Android, Chrome OS, Windows XP, Windows Vista, Windows 7, Windows 8, Windows Server, Windows CE, Unix, Linux, SunOS, Solaris, iOS, Blackberry OS, VxWorks, or other compatible operating systems. In other embodiments, the computing device may be controlled by a proprietary operating system. Conventional operating systems control and schedule computer processes for execution, perform memory management, provide file system, networking, I/O services, and provide a user interface functionality, such as a graphical user interface ("GUI"), among other things.

In some embodiments, the computer system includes a bus or other communication mechanism for communicating information, and a hardware processor, or multiple processors, coupled with the bus for processing information. Hardware processor(s) may be, for example, one or more general purpose microprocessors.

In some embodiments, the computer system may also include a main memory, such as a random access memory (RAM), cache and/or other dynamic storage devices, coupled to a bus for storing information and instructions to be executed by a processor. Main memory also may be used for storing temporary variables or other intermediate information during execution of instructions to be executed by the processor. Such instructions, when stored in storage media accessible to the processor, render the computer system into a special-purpose machine that is customized to perform the operations specified in the instructions.

In some embodiments, the computer system further includes a read only memory (ROM) or other static storage device coupled to bus for storing static information and instructions for the processor. A storage device, such as a magnetic disk, optical disk, or USB thumb drive (Flash drive), etc., may be provided and coupled to the bus for storing information and instructions.

In some embodiments, the computer system may be coupled via a bus to a display, such as a cathode ray tube (CRT) or LCD display (or touch screen), for displaying information to a computer user. An input device, including alphanumeric and other keys, is coupled to the bus for communicating information and command selections to the processor. Another type of user input device is cursor control, such as a mouse, a trackball, or cursor direction keys for communicating direction information and command selections to the processor and for controlling cursor movement on display. This input device typically has two degrees of freedom in two axes, a first axis (e.g., x) and a second axis (e.g., y), that allows the device to specify positions in a plane. In some embodiments, the same direction information and command selections as cursor control may be implemented via receiving touches on a touch screen without a cursor.

In some embodiments, the computing system may include a user interface module to implement a GUI that may be stored in a mass storage device as executable software codes that are executed by the computing device(s). This and other modules may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables.

In general, the word "module," as used herein, refers to logic embodied in hardware or firmware, or to a collection of software instructions, possibly having entry and exit points, written in a programming language, such as, for example, Java, Lua, C or C++. A software module may be compiled and linked into an executable program, installed in a dynamic link library, or may be written in an interpreted programming language such as, for example, BASIC, Perl, or Python. It will be appreciated that software modules may be callable from other modules or from themselves, and/or may be invoked in response to detected events or interrupts. Software modules configured for execution on computing devices may be provided on a computer readable medium, such as a compact disc, digital video disc, flash drive, magnetic disc, or any other tangible medium, or as a digital download (and may be originally stored in a compressed or installable format that requires installation, decompression or decryption prior to execution). Such software code may be stored, partially or fully, on a memory device of the executing computing device, for execution by the computing device. Software instructions may be embedded in firmware, such as an EPROM. It will be further appreciated that hardware modules may be comprised of connected logic units, such as gates and flip-flops, and/or may be comprised of programmable units, such as programmable gate arrays or processors. The modules or computing device functionality described herein are preferably implemented as software modules, but may be represented in hardware or firmware. Generally, the modules described herein refer to logical modules that may be combined with other modules or divided into sub-modules despite their physical organization or storage.

In some embodiments, a computer system may implement the methods described herein using customized hard-wired logic, one or more ASICs or FPGAs, firmware and/or program logic which in combination with the computer system causes or programs the computer system to be a special-purpose machine. According to one embodiment, the methods herein are performed by the computer system in response to hardware processor(s) executing one or more sequences of one or more instructions contained in main memory. Such instructions may be read into main memory from another storage medium, such as a storage device. Execution of the sequences of instructions contained in main memory causes processor(s) to perform the process steps described herein. In alternative embodiments, hard-wired circuitry may be used in place of or in combination with software instructions.

The term "non-transitory media," and similar terms, as used herein refers to any media that store data and/or instructions that cause a machine to operate in a specific fashion. Such non-transitory media may comprise non-volatile media and/or volatile media. Non-volatile media includes, for example, optical or magnetic disks, or other types of storage devices. Volatile media includes dynamic memory, such as a main memory. Common forms of non-transitory media include, for example, a floppy disk, a flexible disk, hard disk, solid state drive, magnetic tape, or any other magnetic data storage medium, a CD-ROM, any other optical data storage medium, any physical medium with patterns of holes, a RAM, a PROM, and EPROM, a FLASH-EPROM, NVRAM, any other memory chip or cartridge, and networked versions of the same.

Non-transitory media is distinct from but may be used in conjunction with transmission media. Transmission media participates in transferring information between nontransitory media. For example, transmission media includes coaxial cables, copper wire and fiber optics, including the wires that comprise a bus. Transmission media can also take the form of acoustic or light waves, such as those generated during radio-wave and infra-red data communications.

Various forms of media may be involved in carrying one or more sequences of one or more instructions to a processor for execution. For example, the instructions may initially be carried on a magnetic disk or solid state drive of a remote computer. The remote computer can load the instructions into its dynamic memory and send the instructions over a telephone line using a modem or other network interface, such as a WAN or LAN interface. A modem local to a computer system can receive the data on the telephone line and use an infra-red transmitter to convert the data to an infra-red signal. An infra-red detector can receive the data carried in the infra-red signal and appropriate circuitry can place the data on a bus. The bus carries the data to the main memory, from which the processor retrieves and executes the instructions. The instructions received by the main memory may retrieve and execute the instructions. The instructions received by the main memory may optionally be stored on a storage device either before or after execution by the processor.

In some embodiments, the computer system may also include a communication interface coupled to a bus. The communication interface may provide a two-way data communication coupling to a network link that is connected to a local network. For example, a communication interface may be an integrated services digital network (ISDN) card, cable modem, satellite modem, or a modem to provide a data communication connection to a corresponding type of telephone line. As another example, a communication interface may be a local area network (LAN) card to provide a data communication connection to a compatible LAN (or WAN component to communicate with a WAN). Wireless links may also be implemented. In any such implementation, a communication interface sends and receives electrical, electromagnetic or optical signals that carry digital data streams representing various types of information.

A network link may typically provide data communication through one or more networks to other data devices. For example, a network link may provide a connection through a local network to a host computer or to data equipment operated by an Internet Service Provider (ISP). The ISP in turn provides data communication services through the world wide packet data communication network now commonly referred to as the "Internet." The local network and Internet both use electrical, electromagnetic or optical signals that carry digital data streams. The signals through the various networks and the signals on the network link and through a communication interface, which carry the digital data to and from the computer system, are example forms of transmission media.

In some embodiments, the computer system can send messages and receive data, including program code, through the network(s), the network link, and the communication interface. In the Internet example, a server might transmit a requested code for an application program through the Internet, ISP, local network, and communication interface.

The received code may be executed by a processor as it is received, and/or stored in a storage device, or other non-volatile storage for later execution.

EXAMPLES

Specific embodiments will be described with reference to the following examples which should be regarded in an illustrative rather than a restrictive sense.

Example 1

Screening of IBD Markers

Figure 1B:
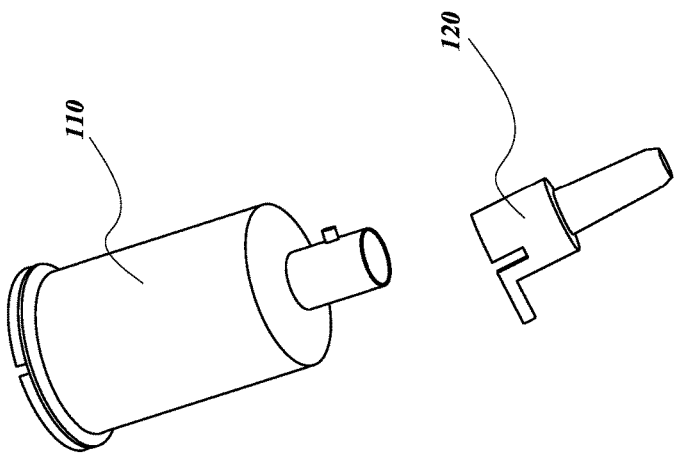
FIG. 1 B depicts an embodiment of a vesicle-capture device.
FIG. 1C depicts an embodiment of a frame for holding a vesicle-capture device in proximity with an oligo(dT)-immobilized plate.
Figure 1B:
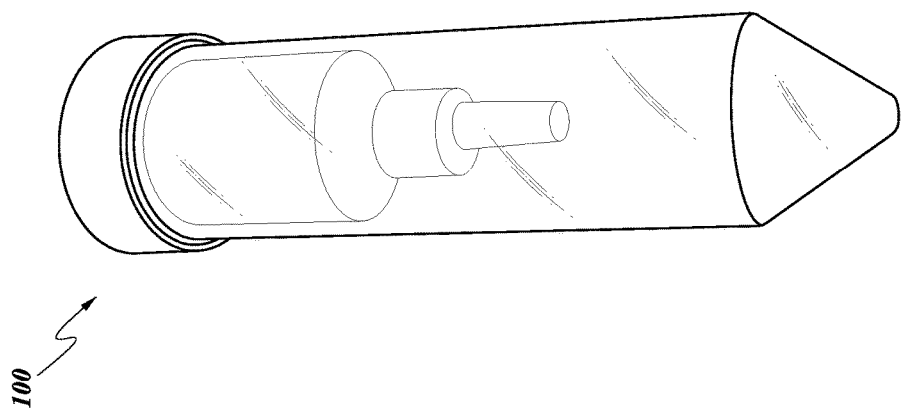
Figure 1C:
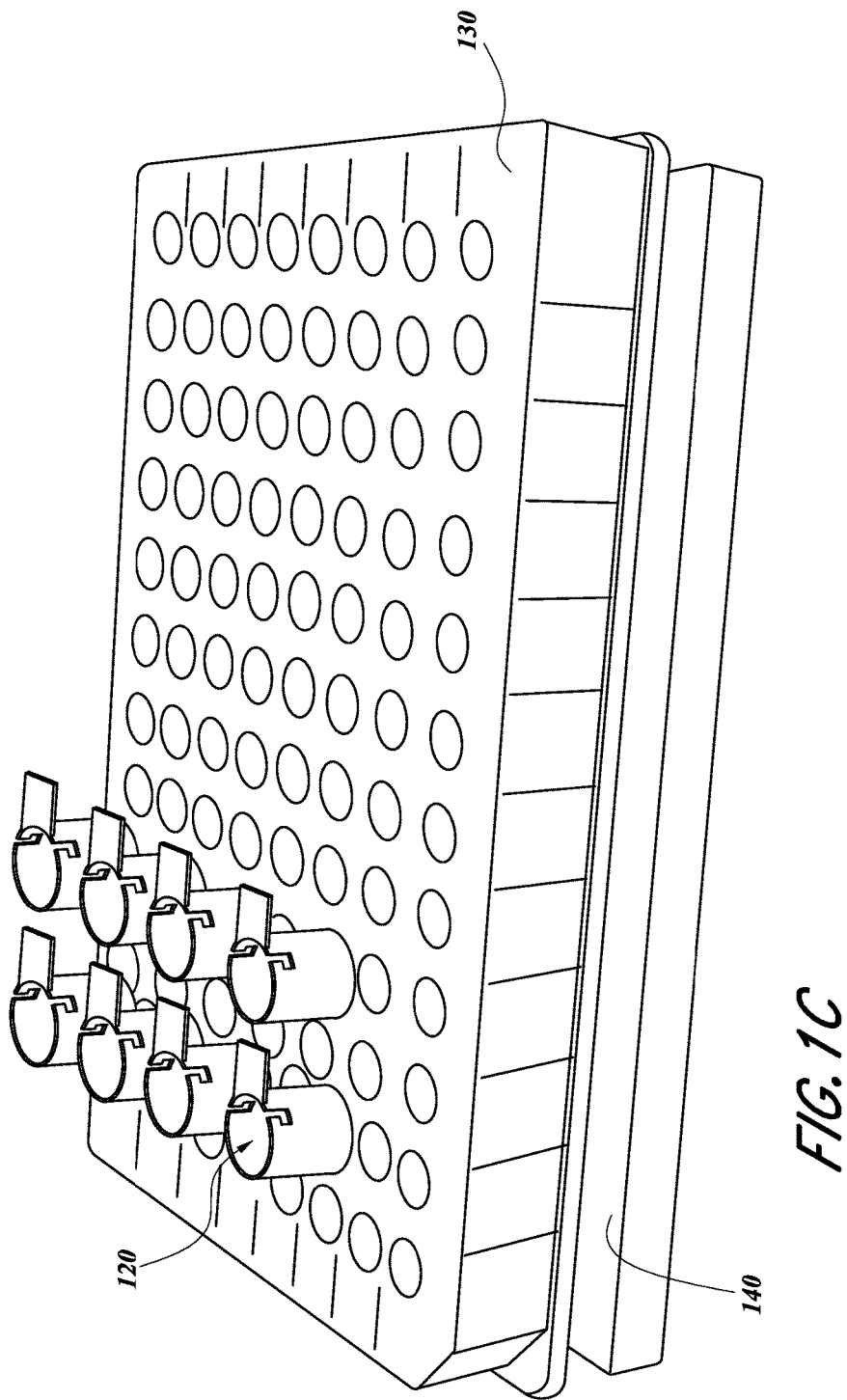

FIGS. 1A-C illustrate devices and methods used to collect EMV from an intestinal luminal fluid (ILF). During routine colonoscopy, ILF was collected from 5 healthy control subjects (HC) and 19 patients with IBD, including 9 ulcerative colitis (UC) and 10 Crohn's disease (CD). During colonoscopy examination, 10 ml of ILF was aspirated through the colonoscopy catheter 10 using a syringe 20 connected to a port of the catheter 10 (FIG. 1A). ILF was mixed with ⅕ volume of 25× phosphate buffered saline to equalize pH and salt concentrations. The equilibrated ILF was then passed through a vesicle-capture device 100 (FIG. 1B). Exosomes and microvesicles (EMV) were isolated from ILF using a vesicle-capture device 100. A 5 mL sample of ILF was loaded into a sample loading region 110 of the vesicle-capture device 100. The vesicle-capture device 100 was subjected to centrifugation (2,000×g, for 5 min), thereby drawing the ILF through a distal tip 120 of the vesicle capture device 100 and causing EMV in the ILF to become entrapped in a vesicle-capture filter housed within the distal tip 120. The distal tip 120 was then detached from the sample loading region 110 and placed in a well of a frame 130 that was set onto an oligo(dT)-immobilized plate 140 (FIG. 1C). Lysis buffer was added to each tip 120 and the tip 120, the frame 130, and the plate 140 were together subjected to centrifugation (2,000×g, for 5 min, at 4° C.). In this way, EMV trapped on or in the filter within the distal tip 120 were lysed to liberate RNA from the EMV. Liberated poly(A)$^+$ mRNA hybridized with the oligo(dT)-immobilized plate 140 and was purified. cDNA was synthesized on the plate 140 from the hybridized poly(A)$^+$ mRNA, and 52 different mRNAs were quantified by reverse transcription polymerase chain reaction (RT-PCR). The results of RT-qPCR were normalized by the values of control mRNA (ACTB) (see Table II).

In a preliminary experiment (discussed in Example 3, below), we confirmed that EMV mRNA was protected even in ILF and stool supernatant, whereas naked mRNA was completely eliminated probably due to the digestion by endogenous ribonucleases (FIG. 3). Various epithelial-, immune/inflammatory-, blood cell-derived-, chemokine-, and miscellaneous mRNAs were successfully detected in ILF EMV. Referring to Table II, another control mRNA (GAPDH) was not different among HC, UC, and CD. Interestingly, 3 epithelial-related genes (EPCAM, MUC2, and TFF1), were significantly lower in IBD than control subjects, whereas 3 leukocyte-derived inflammation-related genes (DEFA3, CD45, TGFB1) and S100A9 were significantly higher in IBD than control (Table II).

Example 2

Capture of EMV from ILF or Stool

Sample Collection from Patients.

After institutional review board (IRB) approval, 10 CD, 9 UC, and 5 healthy control donors (HC) were recruited in a study. The profile of CD and UC was summarized in Table I. ILF was collected during routine colonoscopy, and centrifuged at 2,000×g for 15 min at 4° C. to remove debris and cellular components. The supernatant of ILF was stored at room temperature and processed for EMV isolation on the same day. ILF was mixed with ⅕ volume of 25× phosphate buffered saline (PBS, Life Technologies, Carlsbad, Calif.) to equalize pH and salt concentrations, then applied to the EMV collection filter device 100 (Hitachi Chemical Research Center (HCR), Irvine, Calif.) (FIG. 1B). After centrifugation at 2,000×g at 5 min, filter tips 120 were detached and stored at −80° C. freezer until analysis. For stool EMV analysis, approximately 1 g of fresh stool was mixed with 15 mL 5×PBS, and centrifuged at 2,000×g for 10 min to remove debris and cellular components. The supernatants were used for EMV analysis.

Isolation of EMV by Ultracentrifugation.

ILF, stool suspension, and fetal calf serum (Life) was centrifuged at 2,000×g for 10 min at 4° C. to remove large particles. Then, the supernatants were further centrifuged at 100,000×g for 1 hour at 4° C. to precipitate EMV (XL-90, Beckman Coulter, Fullerton, Calif.) using the Type 90Ti rotor (Beckman). After centrifugation, supernatants were decanted, and the pellets were suspended in phosphate buffered saline (PBS, Life) and multiple aliquots were stored at −80° C. freezer.

Scanning Electron Microscope (SEM).

In order to visualize the captured EMV or EMV-like materials, pooled ILF was applied to the EMV collection filter, and centrifuged at 2,000×g for 5 min. Without any washing, the filter membrane was removed, dried, and analyzed by SEM (S-4800, Hitachi High-Technologies, Tokyo, Japan) without sputter-coating.

Nanoparticle Tracking Analysis.

The particle size distribution of EMV prepared by ultracentrifugation was analyzed by the Nanoparticle tracking device (NanoSight LM20, Amesbury, UK). EMV was visualized by their scattering of a focused laser beam and the collection of the scattered light by a standard optical microscope fitted with a CCD video camera. The software calculated their size using the Stokes-Einstein equation.

As shown in FIG. 2A, EMV-like particles with the size around 100-300 nm were clearly visible on and between the filter fibers. Nanoparticle tracking analysis also demonstrated the nanoparticles with various size from 50-700 nm with the average size of 207+/−12.2 nm in ILF (FIG. 2B) and 214+/−12.3 nm in stool suspension (FIG. 2C), respectively. The shaded area in FIGS. 2B and 2C indicates the mean+/−1 standard error.

Example 3

Stability of EMV mRNA in ILF and Stool

Fetal calf serum-derived purified standard EMV was incubated in ILF, PBS-stool supernatant, or PBS at 37° C. for 30 min, then applied to EMV collection filter device for mRNA isolation, cDNA synthesis followed by PCR as described above. As shown in FIG. 3A, both bovine HBB (light gray bars, FIG. 3A) and GAPDH (black bars, FIG. 3A) mRNAs were preserved during the incubation. In FIG. 3B, naked rat total RNA purchased from Clontech (Mountain View, Calif.) was also incubated with ILF, PBS-stool supernatant, or PBS at 37° C. for 30 min, then 2× Lysis buffer was applied and transferred to oligo(dT)-immobilized microplate for mRNA isolation, cDNA synthesis followed by PCR. As shown in FIG. 3B, rat actb (light gray bars, FIG. 3B) and gapdh (black bars, FIG. 3B) became undetectable after ILF and stool incubation, suggesting that naked mRNA did not stably exist in ILF and stool.

Example 4

EMV mRNA Analysis

After EMV filter tips 120 were placed onto 96-well frame 130 (FIG. 1), 80 µL of Lysis Buffer (HCR) was added and incubated at 37° C. for 10 min to release mRNA from EMV. The 96-well frame 130 was then placed onto oligo(dT)-immobilized plate 140 (FIG. 1), and centrifuged for 5 min at 2000×g at 4° C. The resultant oligo(dT)-immobilized plate 140 was stored at 4° C. overnight for the hybridization between poly(A)$^+$ tail of mRNA and immobilized oligo(dT) as described previously. Next morning, the plate 140 was washed with Wash Buffer (HCR) 6 times to remove non-mRNA materials, then cDNA was directly synthesized in the same microplate 140 by adding dNTPs (final 5 mM), MMLV reverse transcriptase (final 2.7 U/µL), and RNasin (0.13 U/µL) (Life, Carlsbad, Calif.) and incubated at 37° C. for 2 hours. The cDNA was diluted 1:1 with nuclease-free water, and used for subsequent real time SYBR green polymerase chain reaction (PCR) (iTaq, BioRad, Hercules, Calif.) in the final volume of 5 µL in a 384-well plate. Each gene was amplified individually. The PCR condition was 1 cycle of 95° C. for 5 min, followed by 40 cycles of 1 min 95° C. denature and 1 min 65° C. annealing/extension in PRISM7900 (Applied Biosystem, Foster City, Calif.). Melting curve analysis was performed every time to confirm that the amplification was derived from a single peak. The cycle threshold (Ct) was determined by the analytical software (SDS, Applied Biosystem). According to our previous analysis, Ct=32 was used as a baseline. When melting peak was not at right place or multiple peaks were present, these samples were determined as negative, and assigned Ct=32. Primer sequences used in this study were summarized in supplemental Table I.

Statistical Analysis.

To compare mRNA levels between the 2 groups, parametric unpaired t-test was used, when mRNAs were detected from all samples. In contrast, when one of samples was undetected, non-parametric unpaired Mann-Whitney U-test was used. P values<0.05 were considered significant. The statistical analyses were performed using Excel (Microsoft) and Prism 6 (GraphPad Software, La Jolla, Calif.). For the analysis of multiple mRNAs simultaneously, multivariate discriminant analysis was used (Minitab 16, State College, Pa.).

Control housekeeping genes (β-actin, ACTB) and glyceraldehyde-3-phosphate dehydrogenase (GAPDH) were detected from all ILF samples. To normalize the PCR data, all Ct values were subtracted by the Ct of ACTB to calculate ΔCt. Normalized mRNA data (ΔCt against ACTB) were compared among HC, UC, and CD. As shown in Table II, various epithelial-, immune/inflammatory-, blood cell-derived-, chemokine-, and miscellaneous mRNAs were successfully detected in ILF EMV. Interestingly, 3 epithelial-related genes (EPCAM, MUC2, and TFF1), 3 leukocyte-derived inflammation-related genes (DEFA3, CD45, TGFB1) and S100A9 were significantly different between control and UC or CD, whereas no difference was found between UC and CD (Table II). FIG. 4 is a graphic representation of these genes, and clearly demonstrates that the levels of 3 epithelial-related genes (EPCAM, MUC2, and TFF1) were significantly lower (larger ΔCt) in IBD than control subjects, whereas 3 leukocyte-derived inflammation-related genes (DEFA3, CD45, TGFB1) and S100A9 were significantly higher in IBD than control. Only significant results in Table II are shown in FIG. 4, with "t" indicating t-test was used in the statistical analysis and "M" indicating Mann-Whitney test was used in the statistical analysis.

EMV mRNA and Clinical Information.

The values of mRNA (Table II) were compared with the data of patients' information (Table I). The mRNA for EPCAM, MUC2, DEFA3, TGFB, and S100A9 were correlated with the degree of endoscopic score (FIG. 5). Normalized mRNA data (ΔCt against ACTB) were compared with endoscopic score of each patient. Endoscopic scores were as follows: "0" indicates inactive; "1" indicates mild; and "2+" indicates moderate-severe.

Thus, in several embodiments, there are provided methods of characterizing a gastrointestinal condition in a subject or an animal comprising: collecting stool or intestinal luminal fluid from a subject; isolating exosome and/or microvesicles from said stool or intestinal luminal fluid samples; quantifying epithelial- and immune/inflammation-related mRNA in said exosome and/or microvesicles; comparing said presence or levels of said mRNA from said isolated exosome and/or microvesicle population to a reference, wherein a difference of said subject as compared to said reference indicates that said subject may be predisposed to or diagnosed with IBD or abnormal conditions in the gastrointestinal tract.

Additionally, in several embodiments, there are provided methods for monitoring the efficacy of the treatment in a subject or an animal of IBD or abnormal conditions in the gastrointestinal tract comprising: collecting stool or intestinal luminal fluid from a subject twice in a separate day; isolating exosome or microvesicles from said 2 stool or intestinal luminal fluid samples; quantifying epithelial- and immune/inflammation-related mRNA in said exosome or microvesicles; and comparing said presence or levels of said mRNA between said 2 samples, wherein a difference of said mRNA between 2 samples indicates that said subject may be responding or worsening to the treatment.

It is contemplated that various combinations or subcombinations of the specific features and aspects of the embodiments disclosed above may be made and still fall within one or more of the inventions. Further, the disclosure herein of any particular feature, aspect, method, property, characteristic, quality, attribute, element, or the like in connection with an embodiment can be used in all other embodiments set forth herein. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above. Moreover, while the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as "treating a subject for a disease or condition" include "instructing the administration of treatment of a subject for a disease or condition."

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments.

Terms, such as, "first", "second", "third", "fourth", "fifth", "sixth", "seventh", "eighth", "ninth", "tenth", or "eleventh" and more, unless specifically stated otherwise, or otherwise understood within the context as used, are generally intended to refer to any order, and not necessarily to an order based on the plain meaning of the corresponding ordinal number. Therefore, terms using ordinal numbers may merely indicate separate individuals and may not necessarily mean the order therebetween. Accordingly, for example, first and second biomarkers used in this application may mean that there are merely two sets of biomarkers. In other words, there may not necessarily be any intention of order between the "first" and "second" sets of data in any aspects.

The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers. For example, "about 10 nanometers" includes "10 nanometers."

TABLE I

Patient's characteristics.

| | | | | | | | | Therapy | | | |
|---|---|---|---|---|---|---|---|---|---|---|---|
| | # | Gender | Age (y.o) | Duration (years) | Site[*1] | HBI/ SCAI [*2] | ENDO[*3] | Anti- TNF | Steroids | Aza/ 6MP | CRP (mg/L) |
| Control | #1 | Male | 52 | | | | | | | | |
| | #2 | Female | 65 | | | | | | | | |

TABLE I-continued

Patient's characteristics.

| | # | Gender | Age (y.o) | Duration (years) | Site*[1] | HBI/ SCAI *[2] | ENDO*[3] | Anti-TNF | Steroids | Aza/ 6MP | CRP (mg/L) |
|---|---|---|---|---|---|---|---|---|---|---|---|
| | #3 | Female | 60 | | | | | | | | |
| | #4 | Female | 60 | | | | | | | | |
| | #5 | Male | 52 | | | | | | | | |
| UC | #1 | Male | 25 | 5 | 2 | 3 | 1 | N | N | Y | |
| | #2 | Female | 29 | 3 | 2 | 6 | 3 | Y | N | N | 1.6 |
| | #3 | Male | 48 | 6 | 2 | 10 | 2 | N | N | N | 7.7 |
| | #4 | Female | 24 | 4 | 2 | 4 | 1 | N | N | Y | 0.3 |
| | #5 | Male | 47 | 8 | 2 | 3 | 2 | N | N | N | |
| | #6 | Male | 28 | 2 | 2 | 2 | 1 | N | N | N | 0.9 |
| | #7 | Female | 37 | 10 | 2 | 2 | 1 | N | N | Y | 2.5 |
| | #8 | Female | 55 | 21 | 2 | 6 | 2 | N | N | N | 5.1 |
| | #9 | Male | 22 | 6 | 2 | 4 | 1 | N | Y | Y | 1.7 |
| CD | #1 | Female | 35 | 20 | 2 | 6 | 2 | N | N | N | 2.8 |
| | #2 | Female | 35 | 20 | 1 | 8 | 1 | N | N | N | 1.6 |
| | #3 | Male | 47 | 12 | 1 | 5 | 1 | N | N | N | 23.2 |
| | #4 | Female | 43 | 20 | 2 | 6 | 1 | N | Y | N | 1.4 |
| | #5 | Female | 47 | 1 | 2 | 2 | 1 | N | N | Y | 2 |
| | #6 | Male | 74 | 20 | 3 | 2 | 1 | N | N | N | |
| | #7 | Male | 43 | 20 | 3 | 3 | 2 | Y | N | N | 0.5 |
| | #8 | Male | 30 | 9 | 2 | 0 | 1 | Y | Y | Y | 0.6 |
| | #9 | Male | 36 | 9 | 2 | 0 | 0 | Y | Y | Y | 10.8 |
| | #10 | Male | 46 | 5 | 1 | 3 | 2 | Y | N | N | — |

*[1]1: ileum, 2: colon, 3: ileocolon.
*[2]Simple Colitis Activity Index.
*[3]Endoscopic score: 0: inactive, 1: mild, 2: moderate, 3: severe.

TABLE II

Summary of EMV analysis.

| | | | t-test | | | |
|---|---|---|---|---|---|---|
| Category | Gene | Gene name | HC:UC | HC:CD | HC:IBD | UC:CD |
| Control | ACTB | β-actin | | Used for normalization | | |
| | GAPDH | Glyceraldehyde-3-phosphate dehydrogenase | n.s. | n.s. | 0.04 | n.s. |
| Epithelial | MUC2 | Mucin 2 | 0.001 | 0.01 | 0.03 | n.s. |
| | MUC12 | Mucin 12 | n.s. | n.s. | n.s. | n.s. |
| | ICAM | Intercellular adhesion molecule 1 | n.s. | n.s. | n.s. | n.s. |
| | EPCAM | Epithelial cell adhesion molecule | 0.02 | n.s. | 0.02 | n.s. |
| | KRT8 | Keratin 8 | n.s. | n.s. | n.s. | n.s. |
| | EGFR* | Epidermal growth factor receptor | | Not amplified | | |
| | CEACEM8* | Carcinoembryonic antigen-related cell adhesion molecule 8 | n.s. | n.s. | n.s. | n.s. |
| | MMP7* | Matrix metallopeptidase 7 (matrilysin) | | Not amplified | | |
| | TFF1* | Trefoil factor 1 | n.s. | 0.02 | 0.02 | n.s. |
| GI | ALB | Albumin | | Not amplified | | |
| | AMY2A | Pancreatic amylase a2A | | Not amplified | | |
| Immuno-regulatory | IL2 | Interleukin 2 | n.s. | n.s. | n.s. | n.s. |
| | IL4 | Interleukin 4 | | Not amplified | | |
| | IL17 | Interleukin 17 | n.s. | n.s. | n.s. | n.s. |
| | IL27* | Interleukin 27 | | Not amplified | | |
| Inflammatory | TNF | Tumor necrosis factor a | n.s. | n.s. | n.s. | n.s. |
| | TNFSF15 | Tumor necrosis factor superfamily 15 (=TL1A) | | Not amplified | | |
| | DCR3 | Tumor necrosis factor receptor superfamily 6b | n.s. | n.s. | n.s. | n.s. |
| | GZB | Granzyme B | n.s. | n.s. | n.s. | n.s. |
| | MPO | Myeloperoxidase | n.s. | n.s. | n.s. | n.s. |
| | DEFA3 | Defensin α3 | 0.010 | <0.001 | 0.001 | n.s. |
| | TLR4 | Toll like receptor 4 | | Not amplified | | |
| | IFNG | Interferon γ | | Not amplified | | |
| | IRF5* | Interferon regulatory factor 5 | n.s. | n.s. | n.s. | n.s. |
| Anti-inflammatory | IL10 | Interleukin 10 | n.s. | n.s. | n.s. | n.s. |
| | CTLA4 | Cytotoxic T-lymphocyte-associated protein 4 | n.s. | n.s. | n.s. | n.s. |
| | PDL1 | Programmed cell death 1 ligand 1 (CD274) | n.s. | n.s. | n.s. | n.s. |

TABLE II-continued

Summary of EMV analysis.

| Category | Gene | Gene name | t-test HC:UC | t-test HC:CD | t-test HC:IBD | t-test UC:CD |
|---|---|---|---|---|---|---|
| | A52RG1 | Arginase 1 | n.s. | n.s. | n.s. | n.s. |
| | TGFB1 | Transforming growth factor β1 | 0.02 | n.s. | 0.02 | n.s. |
| Blood cells | HBB | Hemoglubin β | n.s. | n.s. | n.s. | n.s. |
| | CD4 | CD4 | n.s. | n.s. | 0.04 | n.s. |
| | CD8 | CD8 | n.s. | n.s. | n.s. | n.s. |
| | CD34 | CD34 | n.s. | n.s. | n.s. | n.s. |
| | CD45 | CD45 | n.s. | n.s. | 0.04 | n.s. |
| | ITGA2B | Integrin, alpha 2β | Not amplified | | | |
| Chemokines | IL6 | Interleukin 6 | n.s. | n.s. | n.s. | n.s. |
| | IL8 | Interleukin 8 | n.s. | n.s. | n.s. | n.s. |
| | CCL20 | C-Cmotif chemokine 20 | n.s. | n.s. | n.s. | n.s. |
| | CXCL14 | C-X-C motif chemokine 14 | Not amplified | | | |
| | CCR9* | C-C motif chemokine receptor 9 | Not amplified | | | |
| Miscellaneous | CD39 | Ectonucleoside triphosphate diphosphohydrolase 1 | n.s. | n.s. | n.s. | n.s. |
| | MRC1* | Mannose receptor, C type 1 | n.s. | n.s. | n.s. | n.s. |
| | CEBPA* | CCAAT/enhancer binding protein (C/EBP), alpha | n.s. | n.s. | n.s. | n.s. |
| | NFKB1* | Nuclear factor of kappa light polypeptide gene enhancer in B-cells 1 | n.s. | n.s. | n.s. | n.s. |
| | HIF1A* | Hypoxia inducible factor 1, α subunit | n.s. | n.s. | n.s. | n.s. |
| | R2RX7* | Purinergic receptor P2X, ligand-gated ion channel, 7 | n.s. | n.s. | n.s. | n.s. |
| | RORC* | RAR-related orphan receptor C | Not amplified | | | |
| | S100A8* | S100 calcium binding protein A8 | 0.040 | n.s. | n,s, | n.s. |
| | S100A9* | S100 calcium binding protein A9 | <0.001 | 0.005 | <0.001 | n.s. |
| | SOCS3* | Suppressor of cytokine signaling 3 | n.s. | n.s. | n.s. | n.s. |

*6 each of UC and CD, and 5 HC were analyzed.

TABLE III

Summary of multivariate discriminant analysis.

| | | Diagnosis HC | Diagnosis UC | Diagnosis CD | Predictive value (%) | | | Diagnosis HC | Diagnosis IBD | Predictive value (%) |
|---|---|---|---|---|---|---|---|---|---|---|
| Prediction | HC | 5 | 1 | 0 | 83.3 | Prediction | HC | 5 | 1 | 83.3 |
| | UC | 0 | 5 | 1 | 83.3 | | IBD | 0 | 18 | 100.0 |
| | CD | 0 | 3 | 9 | 75.0 | | | | | |
| Sensitivity | % | 100 | 55.6 | 90 | | Sensitivity | % | 100 | 94.7 | |
| Parameters | Constant | −36.6 | −9.22 | −6.29 | | | | −31.6 | −7.08 | |
| | EPCAM | 2.62 | 1.74 | 1.28 | | | | 2.12 | 1.39 | |
| | MUC2 | 1.34 | 0.78 | 0.41 | | | | 0.88 | 0.46 | |
| | DEFA3 | 3.35 | 1.24 | 0.50 | | | | 2.49 | 0.59 | |
| | CD45 | 2.22 | 1.01 | 0.74 | | | | 1.95 | 0.80 | |
| | TGF B | −0.01 | 0.28 | 0.52 | | | | 0.33 | 0.52 | |

S100A9 and Tff1 were excluded because only 6 each of UC and CD were analyzed.

SUPPLEMENTAL TABLE I

Primer sequences used in the study.

| Gene | SEQ ID NO: | Forward (5'-3') | SEQ ID NO: | Reverse (5'-3') |
|---|---|---|---|---|
| Human | | | | |
| ACTB | SEQ ID NO: 1 | CCTGGCACCCAGCACAAT | SEQ ID NO: 2 | GCCGATCCACACGGAGTACT |
| GAPDH | SEQ ID NO: 3 | CCCACTCCTCCACCTTTGAC | SEQ ID NO: 4 | CATACCAGGAAATGAGCTTGACAA |
| MUC2 | SEQ ID NO: 5 | GCGGGACATTTGTCATGTACTC | SEQ ID NO: 6 | GATGTGGGTGTAGGTGTGTGTCA |

SUPPLEMENTAL TABLE I-continued

Primer sequences used in the study.

| Gene | SEQ ID NO: | Forward (5'-3') | SEQ ID NO: | Reverse (5'-3') |
|---|---|---|---|---|
| MUC12 | SEQ ID NO: 7 | GCCTTGAGAACGCCTACAACA | SEQ ID NO: 8 | GAGCTCTGTGCCAGAGTCAACA |
| ICAM | SEQ ID NO: 9 | TCCCCCCGGTATGAGATTG | SEQ ID NO: 10 | GCCTGCAGTGCCCATTATG |
| EPCAM | SEQ ID NO: 11 | CAGTTGTTGCTGGAATTGTTGTG | SEQ ID NO: 12 | CATCTCACCCATCTCCTTTATCTCA |
| KRT8 | SEQ ID NO: 13 | CTGGGATGCAGAACATGAGTATTC | SEQ ID NO: 14 | GCTTGTGAGGCCCCCATAG |
| EGFR | SEQ ID NO: 15 | CCTTGCCGCAAAGTGTGTAA | SEQ ID NO: 16 | TGAAGGAGTCACCCCTAAATGC |
| CEACEM8 | SEQ ID NO: 17 | AGTGCAGTGGCACGATCTCA | SEQ ID NO: 18 | AAATTAGCCGGGCGTTGTG |
| MMP7 | SEQ ID NO: 19 | CGGATGGTAGCAGTCTAGGGATT | SEQ ID NO: 20 | GGAATGTCCCATACCCAAAGAA |
| TFF1 | SEQ ID NO: 21 | CCCCAGCACGGTGATTAGTC | SEQ ID NO: 22 | CAGAGCAGTCAATCTGTGTTGTGA |
| ALB | SEQ ID NO: 23 | TGCAAGGCTGACGATAAGGA | SEQ ID NO: 24 | GTAGGCTGAGATGCTTTTAAATGTGA |
| AMY2A | SEQ ID NO: 25 | ACAGAGGATTCATTGTTTTCAACAAT | SEQ ID NO: 26 | ACAGTATGTGCCAGCAGGAAGA |
| IL2 | SEQ ID NO: 27 | GAACTAAAGGGATCTGAAACAACATTC | SEQ ID NO: 28 | TGTTGAGATGATGCTTTGACAAAA |
| IL4 | SEQ ID NO: 29 | CACAGGCACAAGCAGCTGAT | SEQ ID NO: 30 | CCTTCACAGGACAGGAATTCAAG |
| IL17 | SEQ ID NO: 31 | CATGAACTCTGTCCCCATCCA | SEQ ID NO: 32 | TCCAGCCGGAAGGAGTTG |
| IL27 | SEQ ID NO: 33 | CCAAGGCTGGGCACTCAGT | SEQ ID NO: 34 | GATGCCAAGACTCCAGTCCTAAA |
| TNF | SEQ ID NO: 35 | CGAAGGCTCCAAAGAAGACAGT | SEQ ID NO: 36 | CAGGGCAATGATCCCAAAGT |
| TNFSF15 | SEQ ID NO: 37 | TGCGAAGTAGGTAGCAACTGGTT | SEQ ID NO: 38 | CCATTAGCTTGTCCCCTTCTTG |
| DCR3 | SEQ ID NO: 39 | CAATGTGCCAGGCTCTTCCT | SEQ ID NO: 40 | TCACACTCCTCAGCTCCTGGTA |
| GZB | SEQ ID NO: 41 | GCGGTGGCTTCCTGATACAA | SEQ ID NO: 42 | CCAAGGTGACATTTATGGAGCTT |
| MPO | SEQ ID NO: 43 | ACTGCCTGGGTTCCAATCC | SEQ ID NO: 44 | TGTTTAAGGAGGGTAATTTGCTCAA |
| DEFA3 | SEQ ID NO: 45 | CCAGGCTCAAGGAAAAACATG | SEQ ID NO: 46 | CTGGTAGATGCAGGTTCCATAGC |
| TLR4 | SEQ ID NO: 47 | GAAGAGTGAGTGGTGCAAGTATGAA | SEQ ID NO: 48 | ATGGCAGCATCATTGTTCTCATC |
| IFNG | SEQ ID NO: 49 | GGAGACCATCAAGGAAGACATGA | SEQ ID NO: 50 | GCTTTGCGTTGGACATTCAA |
| IRF5 | SEQ ID NO: 51 | CCCCCAGAGCTGGTTGTTAA | SEQ ID NO: 52 | CTGGAGTGTGCAGAGATGACACA |
| IL10 | SEQ ID NO: 53 | GCCATGAGTGAGTTTGACATCTTC | SEQ ID NO: 54 | GATTTTGGAGACCTCTAATTTATGTCCTA |
| CTLA4 | SEQ ID NO: 55 | CACTGAGGTCCGGGTGACA | SEQ ID NO: 56 | GTAGGTTGCCGCACAGACTTC |

SUPPLEMENTAL TABLE I-continued

Primer sequences used in the study.

| Gene | SEQ ID NO: | Forward (5'-3') | SEQ ID NO: | Reverse (5'-3') |
|---|---|---|---|---|
| PDL1 | SEQ ID NO: 57 | TCCAAGAGAGAGGAGAAGCTTTTC | SEQ ID NO: 58 | GCTGTATGGTTTTCCTCAGGATCT |
| ARG1 | SEQ ID NO: 59 | AGACACCAGAAGAAGTAACTCGAACA | SEQ ID NO: 60 | TCCCGAGCAAGTCCGAAAC |
| TGFB1 | SEQ ID NO: 61 | CTGCTGAGGCTCAAGTTAAAAGTG | SEQ ID NO: 62 | TGAGGTATCGCCAGGAATTGT |
| HBB | SEQ ID NO: 63 | GCCCATCACTTTGGCAAAGA | SEQ ID NO: 64 | CCAGCCACCACTTTCTGATAGG |
| CD4 | SEQ ID NO: 65 | AAATGCCACACGGCTCTCA | SEQ ID NO: 66 | GGGTGCTGTGCTTCTGTGAAC |
| CD8 | SEQ ID NO: 67 | CCGAGAGAACGAGGGCTACTATT | SEQ ID NO: 68 | GCACGAAGTGGCTGAAGTACAT |
| CD34 | SEQ ID NO: 69 | CAGGGAAAGGCCAGTGTGAA | SEQ ID NO: 70 | ACCACGTGTTGTCTTGCTGAAT |
| CD45 | SEQ ID NO: 71 | AAGCTCCCTGAAGCAAAGGAA | SEQ ID NO: 72 | GCAGGACCATTGACAGAATGTTC |
| ITGA2B | SEQ ID NO: 73 | TGCTGCTGCTCACCATCCT | SEQ ID NO: 74 | CCGGTTCCGCTTGAAGAAG |
| IL6 | SEQ ID NO: 75 | TCATCACTGGTCTTTTGGAGTTTG | SEQ ID NO: 76 | TCTGCACAGCTCTGGCTTGT |
| IL8 | SEQ ID NO: 77 | TGCTAAAGAACTTAGATGTCAGT | SEQ ID NO: 78 | GCATTGGTCCACTCTCAATCACTCTCA |
| CCL20 | SEQ ID NO: 79 | GATACACAGACCGTATTCTTCATCCTAA | SEQ ID NO: 80 | TGAAAGATGATAGCATTGATGTCACA |
| CXCL14 | SEQ ID NO: 81 | AAGCTGGAAATGAAGCCAAAGT | SEQ ID NO: 82 | ACACGCTCTTGGTGGTGATG |
| CCR9 | SEQ ID NO: 83 | GGATTCCGCTTATTCCTTGGT | SEQ ID NO: 84 | TGCGAACCCAGCTGTTATAATCT |
| CD39 | SEQ ID NO: 85 | CCCAGCTGAGCAACCATTGT | SEQ ID NO: 86 | GACCAGGGAGAATAGAACCATGA |
| MRC1 | SEQ ID NO: 87 | AAAGCTGACACAAGGAAGATGGA | SEQ ID NO: 88 | TCAGGAGGATCACAATGATGACTAC |
| CEBPA | SEQ ID NO: 89 | TTGTACTGTATGCCTTCAGCATTG | SEQ ID NO: 90 | TCGGCTGATAAAGCAAAATATTTG |
| NFKB1 | SEQ ID NO: 91 | GGATCACAGCTGCTTTCTGTTG | SEQ ID NO: 92 | CGACCGTGATACCTTTAATGACAA |
| HIF1A | SEQ ID NO: 93 | TTGCCAGCTCAAAAGAAAACAA | SEQ ID NO: 94 | ACCAACAGGGTAGGCAGAACA |
| R2RX7 | SEQ ID NO: 95 | CTGTGAGGAAGCCCAAGCA | SEQ ID NO: 96 | CAGAATCACCTGAAGGCTTCTTCT |
| RORC | SEQ ID NO: 97 | CGGAAGGCAAGATCAGATCCT | SEQ ID NO: 98 | CCCTGGTGTCCTCCATGCT |
| S100A8 | SEQ ID NO: 99 | GGCCAAGCCTAACCGCTATAA | SEQ ID NO: 100 | CTTCTGAAAGACAGCTGACAAGAGA |
| S100A9 | SEQ ID NO: 101 | CTGAGCTTCGAGGAGTTCATCA | SEQ ID NO: 102 | CGTCACCCTCGTGCATCTT |
| SOCS3 | SEQ ID NO: 103 | GCTAAGAGATTCGCCTTAAATGCT | SEQ ID NO: 104 | CTTGGTGCCCTCCAGTGAGT |

SUPPLEMENTAL TABLE I-continued

Primer sequences used in the study.

| Gene | SEQ ID NO: | Forward (5'-3') | SEQ ID NO: | Reverse (5'-3') |
|---|---|---|---|---|
| Bovine | | | | |
| HBB | SEQ ID NO: 105 | GGCATGAAGCATCTCGATGA | SEQ ID NO: 106 | CAGCTTATCACAGTGCAGCTCACT |
| GAPDH | SEQ ID NO: 107 | AGGTTGTCTCCTGCGACTTCA | SEQ ID NO: 108 | GTGGTCGTTGAGGGCAATG |
| Rat | | | | |
| actb | SEQ ID NO: 109 | TCTGTGTGGATTGGTGGCTCTA | SEQ ID NO: 110 | CTGCTTGCTGATCCACATCTG |
| gapdh | SEQ ID NO: 111 | ACCAGGTTGTCTCCTGTGACTTC | SEQ ID NO: 112 | CAGGAAATGAGCTTCACAAAGTTG |

What is claimed is:

1. A method of treating an inflammatory bowel disease (IBD) in a human subject, the method comprising:
   (A) having a vesicle-containing sample obtained from said human subject sent to a laboratory for the laboratory to perform an assay comprising the following steps (1)-(3):
      (1) capturing at least a portion of vesicles from said sample on or in a vesicle-capture material, thereby generating a vesicle sample;
      (2) quantifying an expression level of at least two genes in said vesicle sample, wherein said at least two genes is selected from the group consisting of epithelial cell adhesion molecule (EPCAM), mucin 2 (MUC2), trefoil factor 1 (TFF1), defensin alpha 3 (DEFA3), lymphocyte common antigen (CD45), transforming growth factor beta 1 (TGFB1), and S100 calcium binding protein A9 (S100A9);
      (3) determining that said subject has said IBD due to said expression level of each of said at least two genes being significantly different from the expression level of the respective gene in a vesicle sample of a healthy human control subject not suffering from said IBD, thereby diagnosing said subject as having IBD; and
   (B) administering an effective amount of an IBD medication to the human subject having said IBD, wherein said IBD medication is selected from the group consisting of an aminosalicylate, a corticosteroid, an immunosuppressor, and a TNF-alpha inhibitor, thereby treating said IBD in said human subject.

2. The method of claim 1, wherein said vesicle-containing sample is selected from the group consisting of a blood sample, a urine sample, a saliva sample, and an intestinal fluid sample.

3. The method of claim 1, wherein capturing comprises passing said vesicle-containing sample through a filter comprising glass fiber.

4. The method of claim 1, further comprising lysing said vesicle sample on or in said vesicle-capture material.

5. The method of claim 1, wherein said inflammatory bowel disease is selected from the group consisting of ulcerative colitis and Crohn's disease.

6. The method of claim 1, wherein said vesicle-containing sample is a stool sample.

7. The method of claim 6, further comprising diluting the stool sample in liquid.

8. The method of claim 1, wherein quantifying an expression level of at least two genes in said vesicle sample comprises quantifying said expression level of three genes.

9. The method of claim 1, wherein the vesicle-containing sample comprises a fluid sample and capturing further comprises:
   receiving said fluid sample; and
   passing said fluid sample through a vesicle capture material adapted to capture a captured vesicle population within said vesicle capture material.

10. The method of claim 9, wherein quantifying comprises:

positioning said vesicle capture material and said captured vesicle population adjacent to a substrate comprising immobilized oligo(dT);

applying lysis buffer to said vesicle capture material, thereby lysing said captured vesicle population;

hybridizing at least two mRNA from said captured vesicle population to said substrate;

synthesizing directly on said substrate at least two cDNA from said at least two mRNA; and quantifying by PCR analysis of said at least two cDNA an expression level of at least two marker mRNA in said captured vesicle population.

11. The method of claim 9, wherein receiving comprises receiving said fluid sample from a medical professional.

12. The method of claim 9, wherein said fluid sample comprises a stool sample from a human being.

13. The method of claim 9, wherein said fluid sample comprises an intraluminal fluid sample from a human being.

14. The method of claim 13, wherein said intraluminal fluid is selected from the group consisting of a blood, a urine, a saliva, and an intestinal fluid.

15. The method of claim 14, wherein said vesicle capture material comprises glass fiber.

16. The method of claim 15, wherein passing comprises loading said fluid sample into a device comprising a loading reservoir removably attached to a tip, wherein said vesicle capture material is housed within said tip.

17. An assay for quantifying an expression level of one or more mRNA in vesicles of an intraluminal fluid sample, the assay comprising:

capturing said vesicles from said intraluminal fluid on a vesicle capture material by passing said intraluminal fluid through said vesicle capture material;

lysing said vesicles on said vesicle capture material, thereby generating a lysate;

passing said lysate from said vesicle capture material to a substrate comprising immobilized oligo(dT);

hybridizing said one or more mRNA from said lysate to said substrate;

synthesizing directly on said substrate cDNA from said one or more mRNA hybridized to said substrate; and using said cDNA for real-time quantitative polymerase chain reaction, thereby quantifying the expression level of said one or more mRNA in said vesicles of said intraluminal fluid sample, wherein each of said one or more mRNA corresponds to a gene selected from the group consisting of epithelial cell adhesion molecule (EPCAM), mucin 2 (MUC2), trefoil factor 1 (TFF1), transforming growth factor beta 1 (TGFB1), and S100 calcium binding protein A9 (S100A9).

* * * * *